United States Patent
Kelly et al.

(10) Patent No.: US 8,426,412 B2
(45) Date of Patent: Apr. 23, 2013

(54) 2-ALKYNYL-6-PYRIDIN-2-YL-PYRIDAZINONES, 2-ALKYNYL-6-PYRIDIN-2-YL-DIHYDRO PYRIDAZINONES, 2-ALKYNYL-6-PYRIMIDIN-2-YL-PYRIDAZINONES AND 2-ALKYNYL-6-PYRIMIDIN-2-YL-DIHYDRO PYRIDAZINONES AND THEIR USE AS FUNGICIDES

(75) Inventors: Martha Kelly, Collegeville, PA (US); Ronald Ross, Jr., Zionsville, IN (US); David H. Young, Carmel, IN (US)

(73) Assignee: Dow AgroSciences, LLC., Indianapolis, IN (US)

( * ) Notice: Subject to any disclaimer, the term of this patent is extended or adjusted under 35 U.S.C. 154(b) by 0 days.

(21) Appl. No.: 12/420,081

(22) Filed: Apr. 8, 2009

(65) Prior Publication Data
US 2009/0253708 A1 Oct. 8, 2009

Related U.S. Application Data

(60) Provisional application No. 61/123,379, filed on Apr. 8, 2008.

(51) Int. Cl.
C07D 401/04 (2006.01)
C07D 403/04 (2006.01)
A61K 31/501 (2006.01)
A01N 63/00 (2006.01)

(52) U.S. Cl.
USPC ............... 514/252.02; 514/252.03; 544/238

(58) Field of Classification Search ............... 544/333; 514/252.2
See application file for complete search history.

(56) References Cited

U.S. PATENT DOCUMENTS

| | | | |
|---|---|---|---|
| 5,726,162 A | 3/1998 | Michelotti et al. | |
| 5,726,176 A | 3/1998 | Michelotti et al. | |
| 5,728,694 A | 3/1998 | Michelotti et al. | |
| 5,728,698 A | 3/1998 | Michelotti et al. | |
| 5,728,715 A | 3/1998 | Michelotti et al. | |
| 5,741,793 A | 4/1998 | Young | |
| 5,855,654 A * | 1/1999 | Willingham et al. | 106/18.32 |
| 2006/0063934 A1 * | 3/2006 | Hagihara et al. | 546/275.4 |

FOREIGN PATENT DOCUMENTS
WO    WO03106385    * 12/2003

OTHER PUBLICATIONS

Xu, et al., Pest Management Science (2006), 62(6), 522-530.*
PCT/ISA/210, International Search Report, Application No. PCT/US2009/039840, Oct. 20, 2009.
PCT/ISA/237, Written Opinion of the International Searching Authority, Application No. PCT/US2009/039840, Oct. 20, 2009.

* cited by examiner

Primary Examiner — Susanna Moore
Assistant Examiner — Cecilia M Jaisle
(74) Attorney, Agent, or Firm — C. W. Arnett

(57) ABSTRACT

This invention relates to certain novel 2-alkynyl-6-pyridin-2-yl-pyridazinones, 2-alkynyl-6-pyridin-2-yl-dihydropyridazinones, 2-alkynyl-6-pyrimidin-2-yl-pyridazinones and 2-alkynyl-6-pyrimidin-2-yl-dihydropyridazinones such as those illustrated in Formula I and to the use of these compounds for control of fungal pathogens of plants and mammals.

Formula I

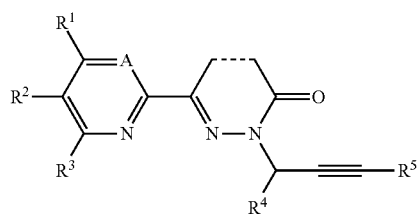

2 Claims, No Drawings

2-ALKYNYL-6-PYRIDIN-2-YL-PYRIDAZINONES, 2-ALKYNYL-6-PYRIDIN-2-YL-DIHYDRO PYRIDAZINONES, 2-ALKYNYL-6-PYRIMIDIN-2-YL-PYRIDAZINONES AND 2-ALKYNYL-6-PYRIMIDIN-2-YL-DIHYDRO PYRIDAZINONES AND THEIR USE AS FUNGICIDES

CROSS-REFERENCE TO RELATED APPLICATIONS

This Application claims the benefit of U.S. Provisional Application 61/123,379 filed on Apr. 8, 2008, which is expressly incorporated by reference herein.

BACKGROUND OF THE INVENTION

This invention relates to certain novel 2-alkynyl-6-pyridin-2-yl-pyridazinones, 2-alkynyl-6-pyridin-2-yl-dihydropyridazinones, 2-alkynyl-6-pyrimidin-2-yl-pyridazinones and 2-alkynyl-6-pyrimidin-2-yl-dihydropyridazinones and to the use of these compounds for control of fungal pathogens of plants and mammals.

A number of dihydropyridazinones and pyridazinones and their pesticidal properties have been described in the art. U.S. Pat. Nos. 5,728,715 and 5,741,793, the disclosures of which are explicitly incorporated by reference herein, disclose a genus of 2-alkynyl-6-aryl dihydropyridazinones and pyridazinones and their use as fungicides. The apparent fungicidal mechanism of action of these compounds involves inhibition of the enzyme Δ-9 fatty acid desaturase as disclosed in WO 03/106385 A2, the disclosure of which is explicitly incorporated by reference herein. One characteristic of these compounds is the ability of some saturated fatty acids to enhance their fungitoxicity towards certain fungi as disclosed in U.S. Pat. No. 5,741,793, the disclosure of which is explicitly incorporated by reference herein. It has now been discovered that a particular subclass of the genus disclosed in '715 and '793 have greatly improved fungicidal activity.

SUMMARY OF THE INVENTION

It has now been found that certain 2-alkynyl-6-pyridin-2-yl-pyridazinones, 2-alkynyl-6-pyridin-2-yl-dihydropyridazinones, 2-alkynyl-6-pyrimidin-2-yl-pyridazinones and 2-alkynyl-6-pyrimidin-2-yl-dihydropyridazinones are superior fungicides with improved control of certain crop diseases and higher potency towards fungal pathogens of mammals.

The invention includes compounds of Formula:

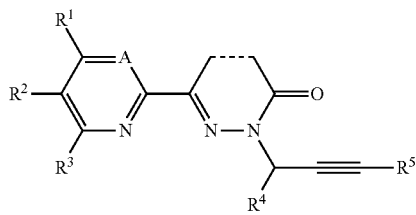

Formula I wherein
A represents N or $CR^6$;
------ represents a single or a double bond;

$R^1$, $R^2$, $R^3$ and $R^6$ independently represent H, halogen, nitro, cyano, $C_1$-$C_6$ alkyl, $C_1$-$C_6$ alkoxy, $C_1$-$C_6$ alkylthio, $C_1$-$C_6$ haloalkyl, $C_1$-$C_6$ haloalkoxy, $C_1$-$C_6$ haloalkylthio, unsubstituted or substituted phenyl, or unsubstituted or substituted phenoxy;
$R^4$ represents H, halogen, cyano or $C_1$-$C_6$ alkyl; and
$R^5$ represents halogen, $C_1$-$C_8$ alkyl, $C_2$-$C_8$ alkenyl, $C_2$-$C_8$ alkynyl, $C_1$-$C_8$ alkoxy, $C_1$-$C_8$ haloalkyl, $C_2$-$C_8$ haloalkenyl, $C_2$-$C_8$ haloalkynyl or $C_1$-$C_8$ haloalkoxy; with the proviso that when A represents $CR^6$, then $R^1$, $R^2$, $R^3$ and $R^6$ are not all H.

The invention includes fungicidal compositions comprising a fungicidally effective amount of a compound of the present invention in admixture with an agriculturally acceptable or pharmaceutically acceptable adjuvant or carrier. The invention also includes a a method of controlling a fungus comprising applying a fungicidally effective amount of a compound of the present invention to the fungus, soil, plant, root, foliage, seed or locus in which the infestation is to be prevented or to the growth medium of said fungus. For pharmaceutical application, the invention also includes a method for treatment or prevention of a fungal infection in a mammal (including humans) which comprises administering a therapeutically effective amount of a compound of the present invention. Dihydropyridazinones and pyridazinones described in U.S. Pat. Nos. 5,728,715 and 5,741,793 also control wood decay fungi such as *Gleophyllum trabeum*, *Phialophora mutabilis*, *Poria palcenta* and *Trametes versicolor*. Accordingly, the present invention also encompasses use of the compounds of the invention as wood preservatives.

DETAILED DESCRIPTION OF THE INVENTION

The compounds of the present invention are characterized as being 2-pyridinyl or 2-pyrimidinyl derivatives of dihydropyridazinones and pyridazinones.

The terms "alkyl", "alkenyl" and "alkynyl", as well as derivative terms such as "alkoxy" and "alkylthio", as used herein, include within their scope straight chain, branched chain and cyclic moieties. The terms "alkenyl" and "alkynyl" are intended to include one or more unsaturated bonds.

The terms "substituted phenyl" and "substituted phenoxy", refers to a phenyl or phenoxy group substituted with one or more substituents selected from halogen, hydroxy, nitro, cyano, formyl, $C_1$-$C_6$ alkyl, $C_2$-$C_6$ alkenyl, $C_2$-$C_6$ alkynyl, $C_1$-$C_6$ alkoxy, $C_1$-$C_6$ alkylthio, $C_1$-$C_6$ haloalkyl, $C_1$-$C_6$ haloalkoxy, $C_1$-$C_6$ haloalkylthio, $C_1$-$C_6$ acyl, $C_1$-$C_6$ alkylsulfinyl, $C_1$-$C_6$ alkylsulfonyl, —OC(O)$C_1$-$C_6$ alkyl, —NHC(O)$C_1$-$C_6$ alkyl, C(O)OH, —C(O)O$C_1$-$C_6$ alkyl, —C(O)NH$_2$, —C(O)NH$C_1$-$C_6$ alkyl, or —C(O)N($C_1$-$C_6$ alkyl)$_2$, provided that the substituents are sterically compatible and the rules of chemical bonding and strain energy are satisfied.

Unless specifically limited otherwise, the term "halogen" including derivative terms such as "halo" refers to fluorine, chlorine, bromine, and iodine.

The terms "haloalkyl", "haloalkenyl", "haloalkynyl", "haloalkoxy" and "haloalkylthio" refer to alkyl, alkenyl, alkynyl, alkoxy and alkylthio groups substituted with from 1 to the maximum possible number of halogen atoms.

The compounds of the present invention can be made using well-known chemical procedures. The required starting materials are commercially available or readily synthesized utilizing standard procedures.

The 2-alkynyl-6-pyridin-2-yl-pyridazinones, 2-alkynyl-6-pyridin-2-yl-dihydropyridazinones, 2-alkynyl-6-pyrimidin-2-yl-pyridazinones and 2-alkynyl-6-pyrimidin-2-yl-dihydropyridazinones can be prepared from a number of ways, which are well known in the art.

As shown in Scheme I, 2-alkynyl-dihydropyridazinones of the present invention can be prepared by cyclization. For example, in step A, di-t-butyl malonate and ethyl chloroacetate can be condensed in the presence of a strong base in a polar aprotic solvent to provide 1,1-di-tert-butyl 2-ethyl ethane-1,1,2-tricarboxylate. In step B, the 1,1-di-tert-butyl 2-ethyl ethane-1,1,2-tricarboxylate can be reacted the appropriate pyridine or pyrimidine acid chloride in the presence of base to provide a tricarboxylate which can be decarboxylated in step C to provide the appropriate ethyl 4-(pyridin-2-yl or pyrimidin-2-yl)-4-oxobutanoate. In step D, the appropriate ethyl 4-(pyridin-2-yl or pyrimidin-2-yl)-4-oxobutanoate can be cyclized with hydrazine to provide the appropriate 6-(pyridin-2-yl or pyrimidin-2-yl)dihydropyridazinone which can be alkylated in step E with an alkyne having an appropriate leaving group (L represents halogen or alkyl or aryl sulfonate).

Scheme I

A.)

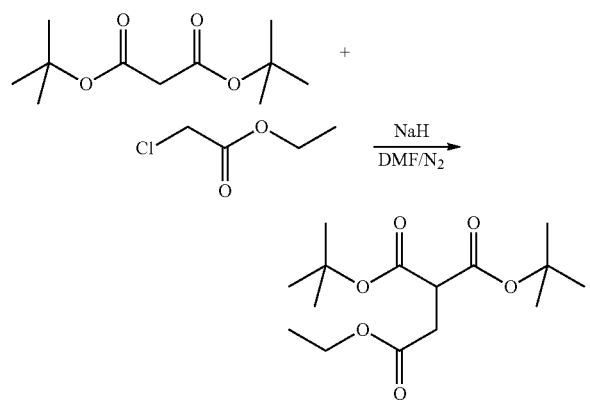

B.)

C.)

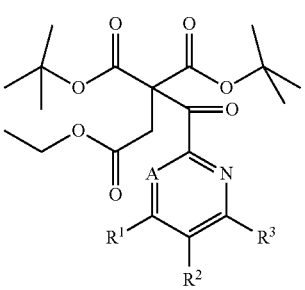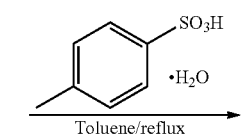

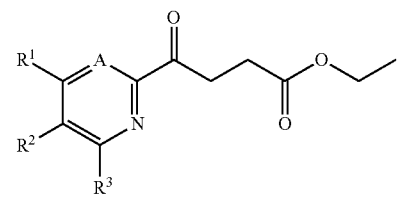

D.)

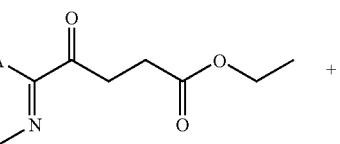

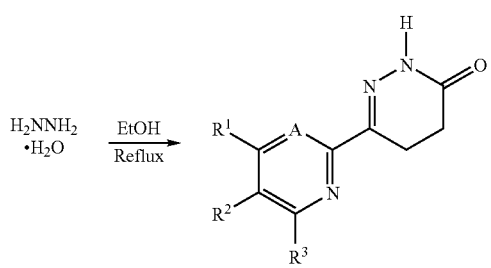

E.)

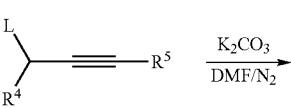

-continued

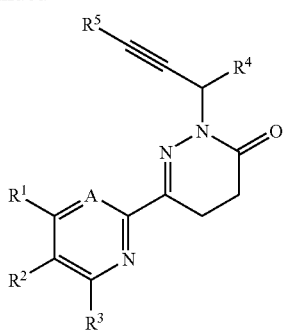

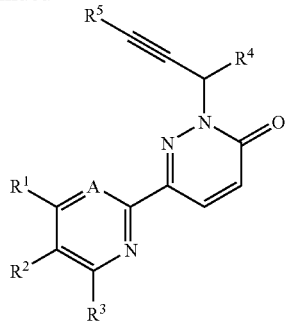

As shown in Scheme II, 6-(pyridin-2-yl or pyrimidin-2-yl) pyridazinones can be prepared from the corresponding 6-(pyridin-2-yl or pyrimidin-2-yl)dihydropyridazinone by bromination-elimination as in step A. The appropriate 6-(pyridin-2-yl or pyrimidin-2-yl)pyridazinone can then be alkylated in step B with an alkyne having an appropriate leaving group (L represents halogen or alkyl or aryl sulfonate).

Alternatively, 6-(pyridin-2-yl or pyrimidin-2-yl)pyridazinones can be prepared directly by cyclization with hydrazine of the glyoxylic acid adduct of the appropriate pyridin-2-yl or pyrimidin-2-yl methyl ketone as shown in Scheme III.

Scheme II

A.)

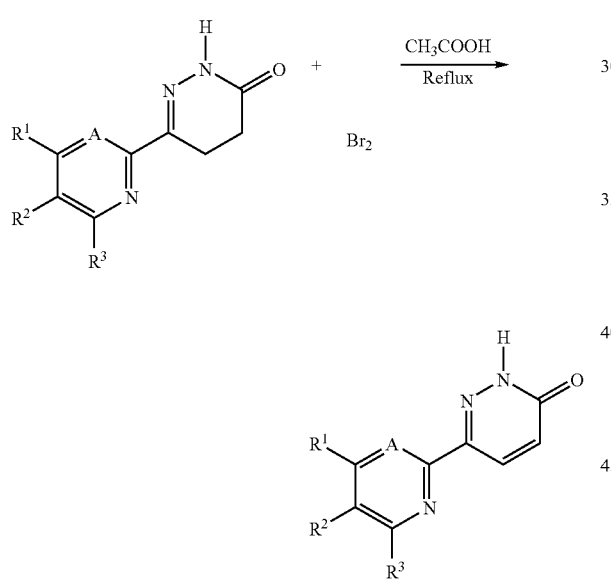

B.)

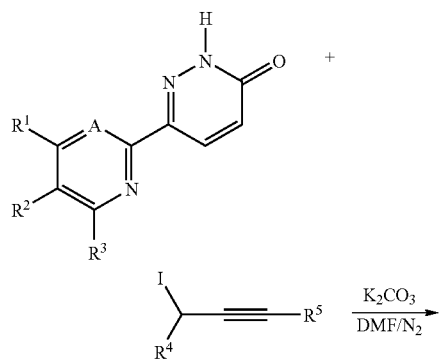

Scheme III

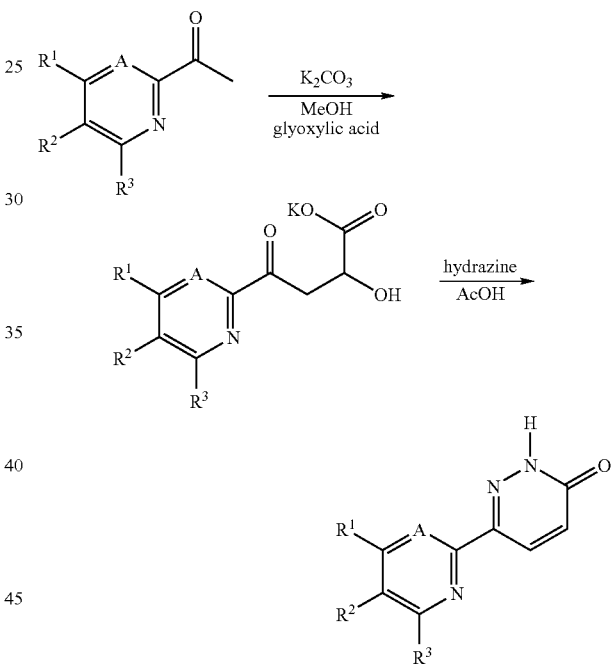

The compounds of the present invention have fungitoxic activity against phytopathogenic fungi, against fungal pathogens of mammals, including humans, and against wood decay causing fungi. They are active against fungi of a number of classes including Deuteromycetes (Fungi Imperfecti), Basidiomycetes, and Ascomycetes. More particularly, the method of this invention provides for activity against phytopathogenic organisms including, but not limited to, *Pyricularia oryzae, Colletotrichum lagenarium, Erysiphe graminis, Puccinia recondita, Helminthosporium* species, *Fusarium* species, *Alternaria solani, Septoria nodorum, Sclerotinia* species, *Sphaerotheca fuliginea, Cercospora* species, *Uncinula necator* and *Podosphaera leucotricha*. More particularly, rice diseases are controlled by the method of the invention. Examples of such rice diseases are seedborne diseases, soilborne diseases, and seedling box and field diseases such as those caused by *Pyricularia oryzae* and *Rhizoctonia* species. Additional diseases include powdery mildew incited by *Sphaerotheca fulignea* (e.g, cucurbit powdery mildew), *Uncinula necator* (e.g., grape powdery mildew), and *Podosphaera leucotricha* (e.g., apple powdery mildew). Cereal diseases are controlled such as those caused by *Erysiphe graminis, Puccinia recondita, Septoria nodurum* and *Helminthosporium* species. Tomato and potato diseases are controlled such as those caused by *Alternaria solani*.

The method of the present invention also provides for activity against fungal pathogens of mammals (including humans) including, but not limited to, *Candida* species such as *C. albicans, C. glabrata, C. parapsilosis, C. krusei*, and *C. tropicalis, Aspergillus* species such as *Aspergillus fumigatus, Fusarium* species, *Coccidioides immitis, Cryptococcus neoformans, Histoplasma capsulatum, Microsporum* species, and *Tricophyton* species. The method of the present invention also provides for activity against fungi which cause wood decay such as *Gleophyllum trabeur, Phialophora mutabilis, Poria palcenta* and *Trametes versicolor*.

The present invention contemplates all vehicles by which the composition of the present invention can be formulated for delivery and use as a pesticide composition, including solutions, suspensions, emulsions, wettable powders and water dispersible granules, emulsifiable concentrates, granules, dusts, baits, and the like. Typically, formulations are applied following dilution of the concentrated formulation with water as aqueous solutions, suspensions or emulsions, or combinations thereof. Such solutions, suspensions or emulsions are produced from water-soluble, water-suspended or water-suspendable, water-emulsified or water-emulsifiable formulations or combinations thereof which are solids, including and usually known as wettable powders or water dispersible granules; or liquids including and usually known as emulsifiable concentrates, aqueous suspensions or suspension concentrates, and aqueous emulsions or emulsions in water, or mixtures thereof such as suspension-emulsions. As will be readily appreciated, any material to which this composition can be added may be used, provided they yield the desired utility without significant interference with the desired activity of the pesticidally active ingredients as pesticidal agents and improved residual lifetime or decreased effective concentration is achieved.

Wettable powders, which may be compacted to form water dispersible granules, comprise an intimate mixture of one or more of the pesticidally active ingredients, an inert carrier and surfactants. The concentration of the pesticidally active ingredient in the wettable powder is usually from about 10 percent to about 90 percent by weight based on the total weight of the wettable powder, more preferably about 25 weight percent to about 75 weight percent. In the preparation of wettable powder formulations, the pesticidally active ingredients can be compounded with any finely divided solid, such as prophyllite, talc, chalk, gypsum, Fuller's earth, bentonite, attapulgite, starch, casein, gluten, montmorillonite clays, diatomaceous earths, purified silicates or the like. In such operations, the finely divided carrier and surfactants are typically blended with the compound(s) and milled.

Emulsifiable concentrates of the pesticidally active ingredient comprise a convenient concentration, such as from about 10 weight percent to about 50 weight percent of the pesticidally active ingredient, in a suitable liquid, based on the total weight of the concentrate. The pesticidally active ingredients are dissolved in an inert carrier, which is either a water miscible solvent or a mixture of water-immiscible organic solvents, and emulsifiers. The concentrates may be diluted with water and oil to form spray mixtures in the form of oil-in-water emulsions. Useful organic solvents include aromatics, especially the high-boiling naphthalenic and olefinic portions of petroleum such as heavy aromatic naphtha. Other organic solvents may also be used, such as, for example, terpenic solvents, including rosin derivatives, aliphatic ketones, such as cyclohexanone, and complex alcohols, such as 2-ethoxyethanol.

Emulsifiers which can be advantageously employed herein can be readily determined by those skilled in the art and include various nonionic, anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxides such as the ethoxylated alkyl phenols and carboxylic esters esterified with the polyol or polyoxyalkylene. Cationic emulsifiers include quaternary ammonium compounds and fatty amine salts. Anionic emulsifiers include the oil-soluble salts (e.g., calcium) of alkylaryl sulfonic acids, oil-soluble salts of sulfated polyglycol ethers and appropriate salts of phosphated polyglycol ether.

Representative organic liquids which can be employed in preparing emulsifiable concentrates are the aromatic liquids such as xylene, propyl benzene fractions; or mixed naphthalene fractions, mineral oils, substituted aromatic organic liquids such as dioctyl phthalate; kerosene; dialkyl amides of various fatty acids, particularly the dimethyl amides; and glycol ethers such as the n-butyl ether, ethyl ether or methyl ether of diethylene glycol, and the methyl ether of triethylene glycol and the like. Mixtures of two or more organic liquids may also be employed in the preparation of the emulsifiable concentrate. Surface-active emulsifying agents are typically employed in liquid formulations and in an amount of from 0.1 to 20 percent by weight based on the combined weight of the emulsifying agents. The formulations can also contain other compatible additives, for example, plant growth regulators and other biologically active compounds used in agriculture.

Aqueous suspensions comprise suspensions of one or more water-insoluble pesticidally active ingredients dispersed in an aqueous vehicle at a concentration in the range from about 5 to about 50 weight percent, based on the total weight of the aqueous suspension. Suspensions are prepared by finely grinding one or more of the pesticidally active ingredients, and vigorously mixing the ground material into a vehicle comprised of water and surfactants chosen from the same types discussed above. Other components, such as inorganic salts and synthetic or natural gums, may also be added to increase the density and viscosity of the aqueous vehicle. It is often most effective to grind and mix at the same time by preparing the aqueous mixture and homogenizing it in an implement such as a sand mill, ball mill, or piston-type homogenizer.

Aqueous emulsions comprise emulsions of one or more water-insoluble pesticidally active ingredients emulsified in an aqueous vehicle at a concentration typically in the range from about 5 to about 50 weight percent, based on the total weight of the aqueous emulsion. If the pesticidally active ingredient is a solid it must be dissolved in a suitable water-immiscible solvent prior to the preparation of the aqueous emulsion. Emulsions are prepared by emulsifying the liquid pesticidally active ingredient or water-immiscible solution thereof into an aqueous medium typically with inclusion of surfactants that aid in the formation and stabilization of the emulsion as described above. This is often accomplished with the aid of vigorous mixing provided by high shear mixers or homogenizers.

The compositions of the present invention can also be granular formulations, which are particularly useful for applications to the soil. Granular formulations usually contain from about 0.5 to about 10 weight percent, based on the total weight of the granular formulation of the pesticidally active ingredient(s), dispersed in an inert carrier which consists entirely or in large part of coarsely divided inert material such as attapulgite, bentonite, diatomite, clay or a similar inexpensive substance. Such formulations are usually prepared by dissolving the pesticidally active ingredients in a suitable solvent and applying it to a granular carrier which has been preformed to the appropriate particle size, in the range of from about 0.5 to about 3 mm. A suitable solvent is a solvent in which the compound is substantially or completely soluble. Such formulations may also be prepared by making a dough or paste of the carrier and the compound and solvent, and crushing and drying to obtain the desired granular particle.

Dusts can be prepared by intimately mixing one or more of the pesticidally active ingredients in powdered form with a suitable dusty agricultural carrier, such as, for example, kaolin clay, ground volcanic rock, and the like. Dusts can suitably contain from about 1 to about 10 weight percent of the compounds, based on the total weight of the dust.

The formulations may additionally contain adjuvant surfactants to enhance deposition, wetting and penetration of the pesticidally active ingredients onto the target site such as a crop or organism. These adjuvant surfactants may optionally be employed as a component of the formulation or as a tank mix. The amount of adjuvant surfactant will typically vary from 0.01 to 1.0 percent by volume, based on a spray-volume of water, preferably 0.05 to 0.5 volume percent. Suitable adjuvant surfactants include, but are not limited to ethoxylated nonyl phenols, ethoxylated synthetic or natural alcohols, salts of the esters of sulfosuccinic acids, ethoxylated organosilicones, ethoxylated fatty amines and blends of surfactants with mineral or vegetable oils.

The formulations may optionally include combinations that contain other pesticidal compounds. Such additional pesticidal compounds may be fungicides, insecticides, nematocides, miticides, arthropodicides, bactericides or combinations thereof that are compatible with the compounds of the present invention in the medium selected for application, and not antagonistic to the activity of the present compounds. Accordingly, in such embodiments, the other pesticidal compound is employed as a supplemental toxicant for the same or for a different pesticidal use. The compounds of the present invention, and the pesticidal compound in the combination can generally be present in a weight ratio of from 1:100 to 100:1.

For pharmaceutical use, the compounds described herein may be taken up in pharmaceutically acceptable carriers, such as, for example, solutions, suspensions, tablets, capsules, ointments, elixirs and injectable compositions. Pharmaceutical preparations may contain from 0.1% to 99% by weight of active ingredient. Preparations which are in single dose form, "unit dosage form", preferably contain from 20% to 90% active ingredient, and preparations which are not in single dose form preferably contain from 5% to 20% active ingredient. As used herein, the term "active ingredient" refers to compounds described herein, salts thereof, and mixtures of compounds described herein with other pharmaceutically active compounds. Dosage unit forms such as, for example, tablets or capsules, typically contain from about 0.05 to about 1.0 g of active ingredient.

Suitable means of administering the pharmaceutical preparations include oral, rectal, topical (including dermal, buccal and sublingual), vaginal, parenteral (including subcutaneous, intramuscular, intravenous, intradermal, intrathecal and epidural) and by naso-gastric tube. It will be understood by those skilled in the art that the preferred route of administration will depend upon the condition being treated and may vary with factors such as the condition of the recipient.

The compounds of the present invention can also be combined with other agricultural fungicides to form fungicidal mixtures and synergistic mixtures thereof. The fungicidal compounds of the present invention are often applied in conjunction with one or more other fungicides to control a wider variety of undesirable diseases. When used in conjunction with other fungicide(s), the presently claimed compounds can be formulated with the other fungicide(s), tank mixed with the other fungicide(s) or applied sequentially with the other fungicide(s). Such other fungicides include amisulbrom 2-(thiocyanatomethylthio)-benzothiazole, 2-phenylphenol, 8-hydroxyquinoline sulfate, antimycin, Ampelomyces, quisqualis, azaconazole, azoxystrobin, *Bacillus subtilis*, benalaxyl, benomyl, benthiavalicarb-isopropyl, benzylaminobenzene-sulfonate (BABS) salt, bicarbonates, biphenyl, bismerthiazol, bitertanol, bixafen, blasticidin-S, borax, Bordeaux mixture, boscalid, bromuconazole, bupirimate, BYF 1047, calcium polysulfide, captafol, captan, carbendazim, carboxin, carpropamid, carvone, chloroneb, chlorothalonil, chlozolinate, *Coniothyrium minitans*, copper hydroxide, copper octanoate, copper oxychloride, copper sulfate, copper sulfate (tribasic), cuprous oxide, cyazofamid, cyflufenamid, cymoxanil, cyproconazole, cyprodinil, coumarin, dazomet, debacarb, diammonium ethylenebis-(dithiocarbamate), dichlofluanid, dichlorophen, diclocymet, diclomezine, dichloran, diethofencarb, difenoconazole, difenzoquat ion, diflumetorim, dimethomorph, dimoxystrobin, diniconazole, diniconazole-M, dinobuton, dinocap, diphenylamine, dithianon, dodemorph, dodemorph acetate, dodine, dodine free base, edifenphos, enestrobin, epoxiconazole, ethaboxam, ethoxyquin, etridiazole, famoxadone, fenamidone, fenarimol, fenbuconazole, fenfuram, fenhexamid, fenoxanil, fenpiclonil, fenpropidin, fenpropimorph, fentin, fentin acetate, fentin hydroxide, ferbam, ferimzone, fluazinam, fludioxonil, flumorph, fluopicolide, fluopyram, fluoroimide, fluoxastrobin, fluquinconazole, flusilazole, flusulfamide, flutolanil, flutriafol, folpet, formaldehyde, fosetyl, fosetyl-aluminium, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), ipconazole, iprobenfos, iprodione, iprovalicarb, isoprothiolane, isotianil, kasugamycin, kasugamycin hydrochloride hydrate, kresoxim-methyl, mancopper, mancozeb, mandipropamid, maneb, mepanipyrim, mepronil, meptyldinocap, mercuric chloride, mercuric oxide, mercurous chloride, metalaxyl, mefenoxam, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxine-copper, oxpoconazole fumarate, oxycarboxin, pefurazoate, penconazole, pencycuron, pentachlorophenol, pentachlorophenyl laurate, penthiopyrad, phenylmercury acetate, phosphonic acid, phthalide, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pyraclostrobin, pyrazophos, pyribencarb, pyributicarb, pyrifenox, pyrimethanil, pyroquilon, quinoclamine, quinoxyfen, quintozene, *Reynoutria sachalinensis* extract, silthiofam, simeconazole, sodium 2-phenylphenoxide, sodium bicarbonate, sodium pentachlorophenoxide, spiroxamine, sulfur, SYP-Z071, SYP-048, SYP-Z048, tar oils, tebuconazole, tecnazene, tetraconazole, thiabendazole, thifluzamide, thiophanate-methyl, thiram, tiadinil, tolclofos-methyl, tolylfluanid, triadimefon, triadimenol, triazolopyrimidine, triazoxide, tricyclazole, tridemorph, trifloxystrobin, triflumizole, triforine, triticonazole, validamycin, vinclozolin, zineb, ziram, zoxamide, *Candida oleophila*, *Fusarium oxysporum*, *Gliocladium* spp., *Phlebiopsis gigantean*, *Streptomyces griseoviridis*, *Trichoderma* spp., (RS)—N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chloro-phenyl)-5-methylrhodanine, 4-(2-nitroprop-1-enyl) phenyl thiocyanateme, ampropylfos, anilazine, azithiram, barium polysulfide, Bayer 32394, benodanil, benquinox, bentaluron, benzamacril; benzamacril-isobutyl, benzamorf, binapacryl, bis(methylmercury) sulfate, bis(tributyltin) oxide, buthiobate, cadmium calcium copper zinc chromate sulfate, carbamorph, CECA, chlobenthiazone, chloraniformethan, chlorfenazole, chlorquinox, climbazole, copper bis(3-phenylsalicylate), copper zinc chromate, cufraneb, cupric hydrazinium sulfate, cuprobam, cyclafuramid, cypendazole, cyprofuram, decafentin, dichlone, dichlozoline, diclobutrazol, dimethirimol, dinocton, dinosulfon, dinoterbon, dipyrithione, ditalimfos, dodicin, drazoxolon, EBP, ESBP, etaconazole, etem, ethirim, fenaminosulf, fenapanil, fenitropan, fluotrimazole, furcarbanil, furconazole, furconazole-cis, furmecyclox, furophanate, glyodine, griseofulvin, halacrinate, Hercules 3944, hexylthiofos, ICIA0858, isopamphos, isovaledione, mebenil, mecarbinzid, metazoxolon, methfuroxam, methylmercury dicyandiamide, metsulfovax, milneb, mucochloric anhydride, myclozolin, N-3,5-dichlorophenyl-succinimide, N-3-nitrophenyl-itaconimide, natamycin, N-ethylmercurio-4-toluenesulfonanilide, nickel bis(dimethyldithiocarbamate), OCH, phenylmercury dimethyldithiocarbamate, phenylmercury nitrate, phosdiphen, prothiocarb; prothiocarb hydrochloride, pyracarbolid, pyridinitril, pyroxychlor, pyroxyfur, quinacetol; quinacetol sulfate, quinazamid, quinconazole, rabenzazole, salicylanilide, SSF-109, sultropen, tecoram, thiadifluor, thicyofen, thiochlorfenphim, thiophanate, thioquinox, tioxymid, triamiphos, triarimol, triazbutil, trichlamide, urbacid, XRD-563, and zarilamid, IK-1140, propargyl amides and any combinations thereof.

The compounds of the present invention can also be combined with other antifungal compounds used to control infections in mammals to form fungicidal mixtures and synergistic mixtures thereof. The fungicidal compounds of the present invention can be applied in conjunction with one or more other antifungal compounds or their pharmaceutically acceptable salts to control a wider variety of undesirable diseases. When used in conjunction with other antifungal compounds, the presently claimed compounds can be formulated with the other antifungal compound(s), coadministered with the other antifungal compound(s) or applied sequentially with the other antifungal compound(s). Typical antifungal compounds include, but are not limited to compounds selected from the group consisting of an azole such as fluconazole, voriconazole, itraconazole, ketoconazole, and miconazole, a polyene such as amphotericin B, nystatin or liposomal and lipid forms thereof such as Abelcet, AmBisome and Amphocil, a purine nucleotide inhibitor such as 5-fluorocytosine, a polyoxin such as nikkomycin, and pneumocandin or echinocandin derivatives such as caspofungin and micofungin.

Additionally, the compounds of the present invention can be combined with other pesticides, including insecticides, nematocides, miticides, arthropodicides, bactericides or combinations thereof that are compatible with the compounds of the present invention in the medium selected for application, and not antagonistic to the activity of the present compounds to form pesticidal mixtures and synergistic mixtures thereof. The fungicidal compounds of the present invention are often applied in conjunction with one or more other pesticides to control a wider variety of undesirable pests. When used in conjunction with other pesticides, the presently claimed compounds can be formulated with the other pesticide(s), tank mixed with the other pesticide(s) or applied sequentially with the other pesticide(s). Typical insecticides include, but are not limited to: antibiotic insecticides such as allosamidin and thuringiensin; macrocyclic lactone insecticides such as spinosad; avermectin insecticides such as abamectin, doramectin, emamectin, eprinomectin, ivermectin and selamectin; milbemycin insecticides such as lepimectin, milbemectin, milbemycin oxime and moxidectin; arsenical insecticides such as calcium arsenate, copper acetoarsenite, copper arsenate, lead arsenate, potassium arsenite and sodium arsenite; botanical insecticides such as anabasine, azadirachtin, d-limonene, nicotine, pyrethrins, cinerins, cinerin I, cinerin II, jasmolin I, jasmolin II, pyrethrin I, pyrethrin II, quassia, rotenone, ryania and sabadilla; carbamate insecticides such as bendiocarb and carbaryl; benzofuranyl methylcarbamate insecticides such as benfuracarb, carbofuran, carbosulfan, decarbofuran and furathiocarb; dimethylcarbamate insecticides dimitan, dimetilan, hyquincarb and pirimicarb; oxime carbamate insecticides such as alanycarb, aldicarb, aldoxycarb, butocarboxim, butoxy-carboxim, methomyl, nitrilacarb, oxamyl, tazimcarb, thiocarboxime, thiodicarb and thiofanox; phenyl methylcarbamate insecticides such as allyxycarb, aminocarb, bufencarb, butacarb, carbanolate, cloethocarb, dicresyl, dioxacarb, EMPC, ethiofencarb, fenethacarb, fenobucarb, isoprocarb, methiocarb, metolcarb, mexacarbate, promacyl, promecarb, propoxur, trimethacarb, XMC and xylylcarb; dinitrophenol insecticides such as dinex, dinoprop, dinosam and DNOC; fluorine insecticides such as barium hexafluorosilicate, cryolite, sodium fluoride, sodium hexafluorosilicate and sulfluramid; formamidine insecticides such as amitraz, chlordimeform, formetanate and formparanate; fumigant insecticides such as acrylonitrile, carbon disulfide, carbon tetrachloride, chloroform, chloropicrin, para-dichlorobenzene, 1,2-dichloropropane, ethyl formate, ethylene dibromide, ethylene dichloride, ethylene oxide, hydrogen cyanide, iodomethane, methyl bromide, methylchloroform, methylene chloride, naphthalene, phosphine, sulfuryl fluoride and tetrachloroethane; inorganic insecticides such as borax, calcium polysulfide, copper oleate, mercurous chloride, potassium thiocyanate and sodium thiocyanate; chitin synthesis inhibitors such as bistrifluoron, buprofezin, chlorfluazuron, cyromazine, diflubenzuron, flucycloxuron, flufenoxuron, hexaflumuron, lufenuron, novaluron, noviflumuron, penfluoron, teflubenzuron and triflumuron; juvenile hormone mimics such as epofenonane, fenoxycarb, hydroprene, kinoprene, methoprene, pyriproxyfen and triprene; juvenile hormones such as juvenile hormone I, juvenile hormone II and juvenile hormone III; moulting hormone agonists such as chromafenozide, halofenozide, methoxyfenozide and tebufenozide; moulting hormones such as α-ecdysone and ecdysterone; moulting inhibitors such as diofenolan; precocenes such as precocene I, precocene II and precocene III; unclassified insect growth regulators such as dicyclanil; nereistoxin analogue insecticides such as bensultap, cartap, thiocyclam and thiosultap; nicotinoid insecticides such as flonicamid; nitroguanidine insecticides such as clothianidin, dinotefuran, imidacloprid and thiamethoxam; nitromethylene insecticides such as nitenpyram and nithiazine; pyridylmethyl-amine insecticides such as acetamiprid, imidacloprid, nitenpyram and thiacloprid; organochlorine insecticides such as bromo-DDT, camphechlor, DDT, pp'-DDT, ethyl-DDD, HCH, gamma-HCH, lindane, methoxychlor, pentachlorophenol and TDE; cyclodiene insecticides such as aldrin, bromocyclen, chlorbicyclen, chlordane, chlordecone, dieldrin, dilor, endosulfan, endrin, HEOD, heptachlor, HHDN, isobenzan, isodrin, kelevan and mirex; organophosphate insecticides such as bromfenvinfos, chlorfenvinphos, crotoxyphos, dichlorvos, dicrotophos, dimethylvinphos, fospirate, heptenophos, methocrotophos, mevinphos, monocrotophos, naled, naftalofos, phosphamidon, propaphos, TEPP and tetrachlorvinphos; organothiophosphate insecticides such as dioxabenzofos, fosmethilan and phenthoate; aliphatic organothiophosphate insecticides such as acethion, amiton, cadusafos, chlorethoxyfos, chlormephos, demephion, demephion-O, demephion-S, demeton, demeton-O, demeton-S, demeton-methyl, demeton-O-methyl, demeton-S-methyl, demeton-S-methylsulphon, disulfoton, ethion, ethoprophos, IPSP, isothioate, malathion, methacrifos, oxydemeton-methyl, oxydeprofos, oxydisulfoton, phorate, sulfotep, terbufos and thiometon; aliphatic amide organothiophosphate insecticides such as amidithion, cyanthoate, dimethoate, ethoate-methyl, formothion, mecarbam, omethoate, prothoate, sophamide and vamidothion; oxime organothiophosphate insecticides such as chlorphoxim, phoxim and phoxim-methyl; heterocyclic organothiophosphate insecticides such as azamethiphos, coumaphos, coumithoate, dioxathion, endothion, menazon, morphothion, phosalone, pyraclofos, pyridaphenthion and quinothion; benzothiopyran organothiophosphate insecticides such as dithicrofos and thicrofos; benzotriazine organothiophosphate insecticides such as azinphos-ethyl and azinphos-methyl; isoindole organothiophosphate insecticides such as dialifos and phosmet; isoxazole organothiophosphate insecticides such as isoxathion and zolaprofos; pyrazolopyrimidine organothiophosphate insecticides such as chlorprazophos and pyrazophos; pyridine organothiophosphate insecticides such as chlorpyrifos and chlorpyrifos-methyl; pyrimidine organothiophosphate insecticides such as butathiofos, diazinon, etrimfos, lirimfos, pirimiphos-ethyl, pirimiphos-methyl, primidophos, pyrimitate and tebupirimfos; quinoxaline organothiophosphate insecticides such as quinalphos and quinalphos-methyl; thiadiazole organothiophosphate insecticides such as athidathion, lythidathion, methidathion and prothidathion; triazole organothiophosphate insecticides such as isazofos and triazophos; phenyl organothiophosphate insecticides such as azothoate, bromophos, bromophos-ethyl, carbophenothion, chlorthiophos, cyanophos, cythioate, dicapthon, dichlofenthion, etaphos, famphur, fenchlorphos, fenitrothion fensulfothion, fenthion, fenthion-ethyl, heterophos, jodfenphos, mesulfenfos, parathion, parathion-methyl, phenkapton, phosnichlor, profenofos, prothiofos, sulprofos, temephos, trichlormetaphos-3 and trifenofos; phosphonate insecticides such as butonate and trichlorfon; phosphonothioate insecticides such as mecarphon; phenyl ethylphosphonothioate insecticides such as fonofos and trichloronat; phenyl phenylphosphonothioate insecticides such as cyanofenphos, EPN and leptophos; phosphoramidate insecticides such as crufomate, fenamiphos, fosthietan, mephosfolan, phosfolan and pirimetaphos; phosphoramidothioate insecticides such as acephate, isocarbophos, isofenphos, methamidophos and propetamphos; phosphorodiamide insecticides such as dimefox, mazidox, mipafox and schradan; oxadiazine insecticides such as indoxacarb; phthalimide insecticides such as dialifos, phosmet and tetramethrin; pyrazole insecticides such as acetoprole, cyenopyrafen, ethiprole, fipronil, pyrafluprole, pyriprole, tebufenpyrad, tolfenpyrad and vaniliprole; pyrethroid ester insecticides such as acrinathrin, allethrin, bioallethrin, barthrin, bifenthrin, bioethanomethrin, cyclethrin, cycloprothrin, cyfluthrin, beta-cyfluthrin, cyhalothrin, gamma-cyhalothrin, lambda-cyhalothrin, cypermethrin, alpha-cypermethrin, beta-cypermethrin, theta-cypermethrin, zeta-cypermethrin, cyphenothrin, deltamethrin, dimefluthrin, dimethrin, empenthrin, fenfluthrin, fenpirithrin, fenpropathrin, fenvalerate, esfenvalerate, flucythrinate, fluvalinate, tau-fluvalinate, furethrin, imiprothrin, metofluthrin, permethrin, biopermethrin, transpermethrin, phenothrin, prallethrin, profluthrin, pyresmethrin, resmethrin, bioresmethrin, cismethrin, tefluthrin, terallethrin, tetramethrin, tralomethrin and transfluthrin; pyrethroid ether insecticides such as etofenprox, flufenprox, halfenprox, protrifenbute and silafluofen; pyrimidinamine insecticides such as flufenerim and pyrimidifen; pyrrole insecticides such as chlorfenapyr; tetronic acid insecticides such as spiromesifen; thiourea insecticides such as diafenthiuron; urea insecticides such as flucofuron and sulcofuron; and unclassified insecticides such as closantel, crotamiton, EXD, fenazaflor, fenoxacrim, flubendiamide, hydramethylnon, isoprothiolane, malonoben, metaflumizone, metoxadiazone, nifluridide, pyridaben, pyridalyl, rafoxanide, triarathene, triazamate, meptyldinocap, pyribencarb and any combinations thereof.

The compounds of the present invention can also be combined with fatty acids such as palmitic and pentadecanoic acids as well as salts or esters thereof. Such mixtures may demonstrate synergistic activity towards fungal pathogens.

The compounds have broad ranges of efficacy as fungicides. The exact amount of the active material to be applied is dependent not only on the specific active material being applied, but also on the particular action desired, the fungal species to be controlled, and the stage of growth thereof, as well as the part of the plant or other product to be contacted with the compound. Thus, all the compounds, and formulations containing the same, may not be equally effective at similar concentrations or against the same fungal species.

The compounds are effective in use with plants in a disease-inhibiting and phytologically acceptable amount. The term "disease inhibiting and phytologically acceptable amount" refers to an amount of a compound that kills or inhibits the plant disease for which control is desired, but is not significantly toxic to the plant. This amount will generally be from about 0.1 to about 1000 ppm (parts per million), with 1 to 500 ppm being preferred. The exact concentration of compound required varies with the fungal disease to be controlled, the type of formulation employed, the method of application, the particular plant species, climate conditions, and the like. The dilution and rate of application will depend upon the type of equipment employed, the method and frequency of application desired and diseases to be controlled, but the effective amount is usually from about 0.01 kilogram (kg) to about 20 kg, of active ingredient (a.i.) per hectare (ha). As a foliar fungicide, a compound of the present invention is usually applied to growing plants at a rate of about 0.1 to about 5 and preferably from about 0.125 to about 0.5 kg per hectare.

As a seed protectant, the amount of toxicant coated on the seed is usually at a dosage rate of about 10 to about 250 grams (g) and preferably from about 20 to about 60 g per 50 kilograms of seed. As a soil fungicide, the chemical can be incorporated in the soil or applied to the surface usually at a rate of 0.5 to about 20 kg and preferably about 1 to about 5 kg per hectare.

In particular, the compounds effectively control a variety of undesirable fungi that infect useful plant crops. Activity has been demonstrated for a variety of fungi, including those causing following the following plant diseases: Anthracnose of Cucumber (*Collatotrichum lagenarium*—COLLLA); Rice Blast (*Pyricularia oryzae*—PYRIOR); Leaf Rust of Wheat (*Puccinia recondite tritici*—PUCCRT); Powdery Mildew of Cucumber (*Erysiphe cichoracearum*—ERYSCI) and Glume Blotch of Wheat (*Septoria nodorum*—LEPTNO).

Additionally, the compounds are active against a variety of fungi that infect mammals. Activity has been demonstrated for a variety of such pathogens, including *Candida albicans, C. glabrata, C. parapsilosis, C. krusei,* and *C. tropicalis, Aspergillus fumigatus,* and *Cryptococcus neoformans*. Furthermore, the compounds are active against azole-resistant strains.

It will be understood by those in the art that the efficacy of the compound on the foregoing plant and mammalian pathogens establishes the general utility of the compounds as fungicides and antifungals.

The following Examples are presented to illustrate the various aspects of this invention and should not be construed as limitations to the claims.

PREPARATION EXAMPLES

1. Preparation of 6-(5-chloropyridin-2-yl)-2-pent-2-ynyl-4,5-dihydropyridazin-3(2H)-one Compound 3

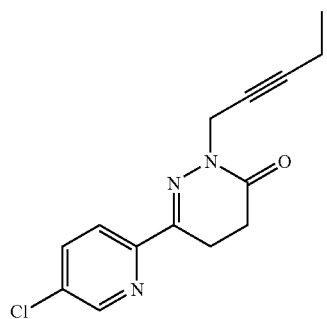 [SMILES: CCC#CCN1N=C(c2ccc(Cl)cn2)CCC1=O]

A. 1,1-Di-tert-butyl 2-ethyl ethane-1,1,2-tricarboxylate

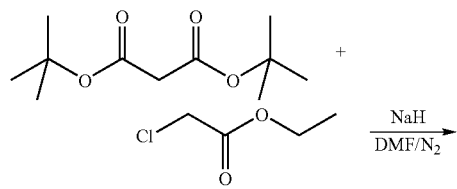

-continued

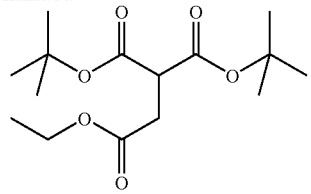

To a dry 1000 ml flask equipped with magnetic stirrer, nitrogen inlet, addition funnel, and thermometer was charged 9.3 grams (g) 60% sodium hydride (0.231 mol) and aprox. 400 milliliters (mL) of dry dimethyl formamide (DMF). The slurry was cooled to 5° C. with an ice water bath, and 50 g di-t-butyl malonate (0.231 mol) was added dropwise in about 25 mL of dry DMF at a rate that maintained the temperature below 10° C. (about 30 minutes, gas evolution, and a fair amount of foaming occurs). The cooling bath was removed and the reaction was warmed to ambient temperature for about 10 minutes, then re-cooled to 5° C. Ethyl chloroacetate (24.7 g; 0.231 mol) was then added dropwise in about 25 mL of DMF at a rate which maintained the temperature below 10° C. (about 10 minutes). The reaction was allowed to slowly warm to ambient temperature, while stirring under nitrogen overnight.

An aliquot was analyzed by GC, which indicated about 70% desired product, with about 15% dialkylated, and 15% unalkylated. The reaction was carefully quenched with about 200 mL of water, and extracted with 3×100 mL of diethyl ether. The combined ether extract was washed with 100 mL of water, 100 mL of saturated aqueous sodium chloride solution, dried over anhydrous magnesium sulfate, filtered, and stripped. Afforded 63 g of a yellowish liquid which was fractionally distilled at ~0.5 mm Hg. The pure fractions were combined to afford 41 g of a clear colorless liquid, which was 97% pure by GC. The NMR data is as follows: 300 MHz $^1$H NMR (CDCl3, TMS=0 ppm) 1.25 (t, 3H); 1.48 (s, 18H); 2.05 (d, 2H); 3.65 (t, 1H); 4.15 (q, 2H). The sample was stored in the refrigerator and had 59% isolated yield.

B. 5-Chloropyridine-2-carbonyl chloride

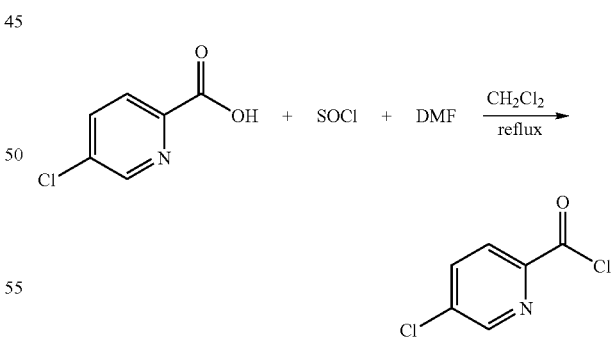

To a dry 250 mL round-bottom flask equipped with magnetic stirrer and reflux condenser was charged 5 g of 5-chloropyridine-2-carboxylic acid (0.0317 mol), 100 mL methylene chloride, and 5 drops of DMF as a catalyst. Some of the solid did not dissolve. Thionyl chloride (10 mL; 0.137 mol) was added in one portion, and the reaction was refluxed for a total of 7 hours. After cooling, the reaction was stripped to dryness and 5.1 g of a white solid was isolated. The NMR data is as follows: 300 MHz $^1$H NMR (CDCl3, TMS=0 ppm) 1.25

(t, 3H); 1.48 (s, 18H); 2.05 (d, 2H); 3.65 (t, 1H); 4.15 (q, 2H). The sample was stored in the refrigerator and had 59% isolated yield. The sample was used without additional purification and had 91% isolated yield.

C. 1,1-Di-tert-butyl 2-ethyl-2-(5-chloropyridin-2-yl)-ethane-1,1,2-tricarboxylate

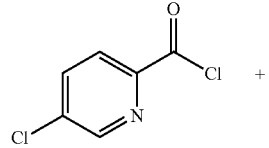

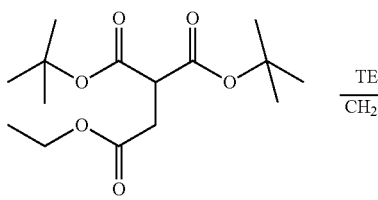

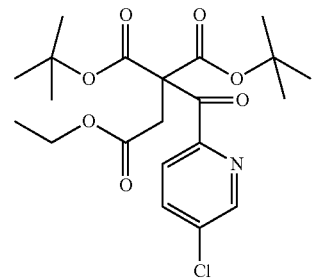

To a dry 500 mL flask equipped with magnetic stirrer, nitrogen inlet, addition funnel, and thermometer was charged 8.6 g 1,1-di-tert-butyl 2-ethyl ethane-1,1,2-tricarboxylate (0.028 mol), 200 mL of methylene chloride, and 7.9 mL of triethyl amine. The solution was stirred under nitrogen at ambient temperature as 5.0 g of 5-chloropyridine-2-carbonyl chloride (0.028 mol) dissolved in about 5 mL of methylene chloride was added dropwise at rate which maintained the temperature below 30° C. The reaction was stirred overnight at ambient temperature under nitrogen. An aliquot was analyzed by GC, which indicated that the reaction was essentially complete. The contents of the flask were transferred to a 1000 mL sep. funnel, and an additional 200 mL of methylene chloride was added. The methylene chloride solution was washed with 2×100 mL of water, 100 mL of saturated aqueous sodium chloride solution, dried over anhydrous magnesium sulfate, filtered, and stripped to afford 9.9 g of a pale yellow liquid which was predominately the desired product. The NMR data is as follows: 300 MHz $^1$H NMR (CDCl3, TMS=0 ppm) 1.25 (t, 3H); 1.48 (s, 18H); 3.50 (s, 2H); 4.15 (q, 2H); 7.85 (d, 1H); 8.10 (d, 1H); 8.6 (s, 1H). The sample was used without additional purification and had 80% isolated yield.

D. Ethyl 4-(5-chloropyridin-2-yl)-4-oxobutanoate

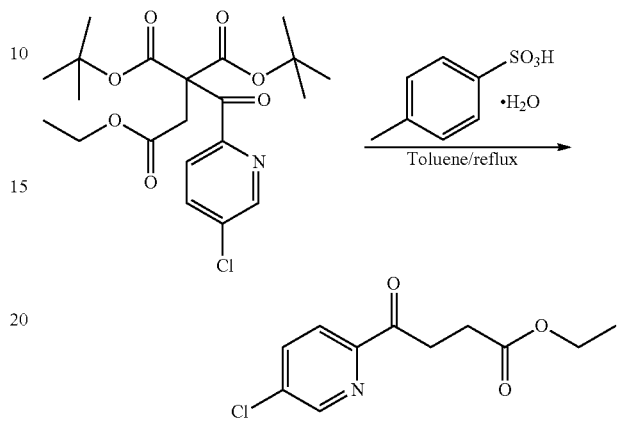

To a dry 250 mL round-bottom flask equipped with magnetic stirrer and reflux condenser was charged 9.9 g of 1,1-di-tert-butyl 2-ethyl-2-(5-chloropyridin-2-yl)-ethane-1,1,2-tricarboxylate (0.0224 mol), 150 mL of toluene, and 1.0 g of p-toluene sulfonic acid mono hydrate (0.0052 mol). The reaction was heated to reflux, and refluxing was continued until no starting material was detected by GC and TLC (a total of about 5 hours) The reaction was cooled to ambient temp, and poured in about 200 mL of water. The reaction was extracted with 3×100 mL of ethyl ether, and the combined organic extract was washed with 100 mL of water, 100 mL of saturated aqueous sodium chloride solution, dried over anhydrous magnesium sulfate, filtered, and stripped to afford 9.2 g of a dark liquid which appeared to be a mixture of the desired product and toluene (about 40% ketoester by NMR). The NMR data is as follows: 300 MHz $^1$H NMR (CDCl3, TMS=0 ppm) 1.30 (t, 3H); 2.80 (t, 2H); 3.60 (t, 2H), 4.20 (q, 2H); 7.85 (d, 1H); 8.10 (d, 1H); 8.70 (s, 1H). The sample was used without additional purification. Estimated yield ~70%.

E. 6-(5-Chloropyridin-2-yl)-4,5-dihydropyridazin-3(2H)-one

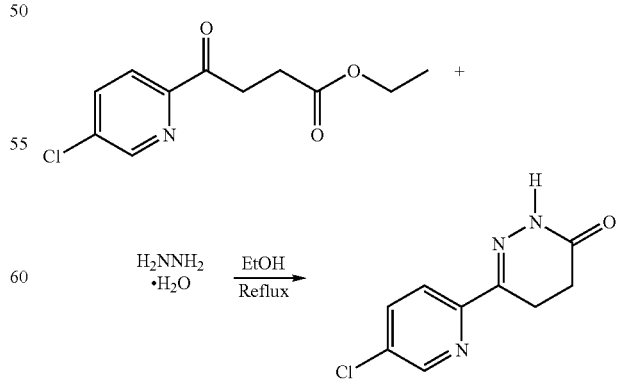

To a dry 200 mL flask equipped with magnetic stirrer, and reflux condenser was charged 3.7 g ethyl 4-(5-chloropyridin- 2-yl)-4-oxobutanoate (0.0153 mol), 75 mL ethanol, and 0.8 g of hydrazine hydrate (0.0168 mol). The reaction was heated at reflux for about 2 hours. An aliquot was analyzed by GC which indicated no remaining starting material, and one major product. The reaction was cooled and poured into about 200 mL of water to afford a tan solid which was collected by vacuum filtration, washed with water, hexane, and dried overnight in vacuo at 40° C. Isolated 2.6 g of a tan solid. The NMR data is as follows: 300 MHz $^1$H NMR (CDCl3, TMS=0 ppm) 2.65 (t, 2H); 3.22 (t, 2H), 7.75 (d, 1H); 8.00 (d, 1H); 8.60 (s, 1H); 8.70 (bs, 1H). The sample was stored in the refrigerator and had 81% isolated yield.

F. 6-(5-chloropyridin-2-yl)-2-pent-2-ynyl-4,5-dihydropyridazin-3(2H)-one

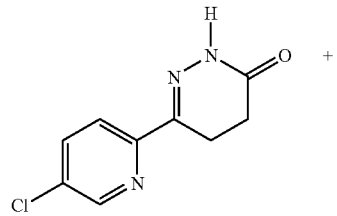

To a 100 mL 3 neck flask equipped with magnetic stirrer, addition funnel, and nitrogen inlet was charged 200 milligrams (mg) of 6-(5-chloropyridin-2-yl)-4,5-dihydropyridazin-3(2H)-one (0.95 mmol), 3.8 mg of 60% sodium hydride (oil dispersion) (0.95 mmol), and 20 mL of dry DMF. The reaction mixture was stirred for about 30 minutes at ambient temperature followed by the dropwise addition of 0.1 ml of pentynyl chloride (0.95 mmol) in about 5 mL of dry DMF. The reaction was stirred overnight at ambient temperature, and checked by TLC and GC the next morning. No starting material remained, and one new product was formed. The reaction was poured into about 100 mL of water, and extracted with 3×50 mL of ethyl acetate. The combined ether extract was washed with 100 mL of water, 100 mL of saturated aqueous sodium chloride solution, dried, and stripped to afford 240 mg of a tan solid 92% isolated yield. The NMR data is a 1 follows: 300 MHz $^1$H NMR (CDCl3, TMS=0 ppm) 1.15 (t, 3H); 2.20 (m, 2H); 2.60 (t, 2H); 3.25 (t, 2H); 4.70 (s, 2H); 7.75 (d, 1H); 8.15 (d, 1H); 8.50 (s, 1H).

Example 2

Preparation of 6-(5-chloropyridin-2-yl)-2-pent-2-ynylpyridazin-3(2H)-one

Compound 8 Method I

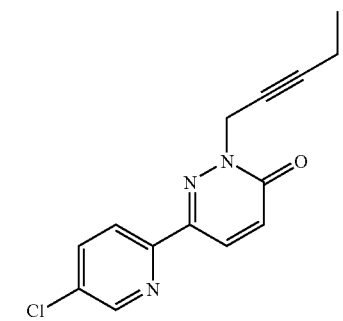 [SMILES: CCC#CCn1nc(-c2ccc(Cl)cn2)ccc1=O]

A. 6-(5-Chloropyridin-2-yl)pyridazin-3(2H)-one

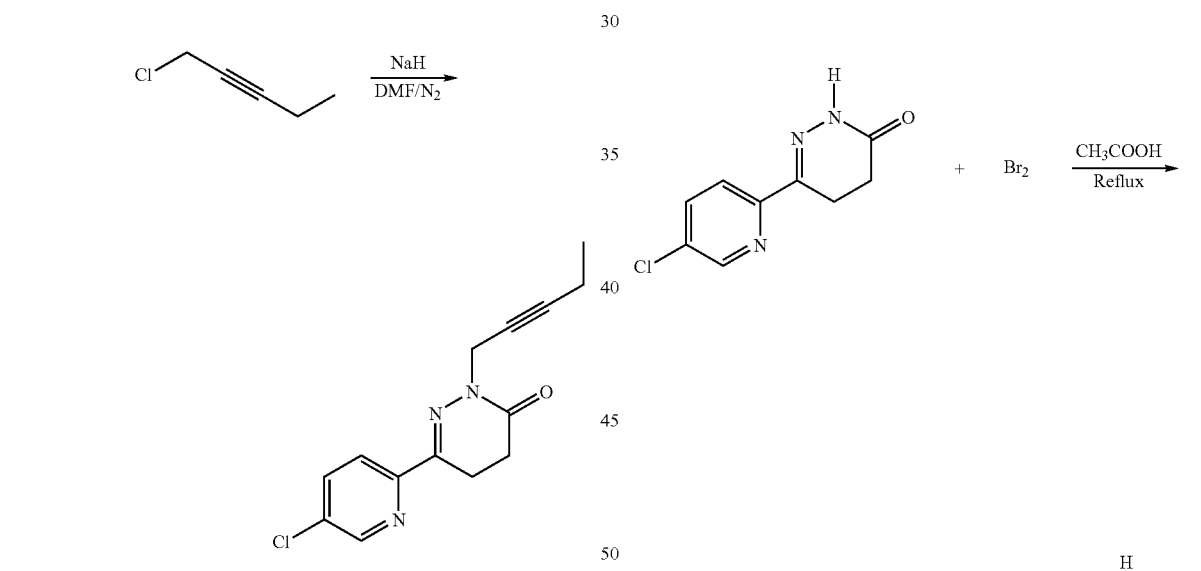

To a dry 100 mL flask equipped with magnetic stirrer and reflux condenser was charged 2.0 g of 6-(5-chloropyridin-2-yl)-4,5-dihydropyridazin-3(2H)-one (0.00955 mol), and about 25 mL of glacial acetic acid (some solid did not dissolve). Bromine (0.5 mL; 0.00955 mol) was added in one portion, and the reaction was slowly heated to reflux. After about 15 minutes at reflux, the color discharged. An aliquot was analyzed by TLC which revealed no starting material remained, and one major product was formed. The reaction was cooled and stirred at ambient temperature overnight. The reaction mixture was poured into about 300 mL of water, and stirred to afford a tan solid which was collected by vacuum filtration, washed with water, hexane, and dried in vacuo at 40° C. overnight. Isolated 1.9 g of a tan solid was isolated. The NMR data is as follows: 300 MHz $^1$H NMR (DMSO d-6, TMS=0 ppm) 7.10 (d, AH); 7.75 (d, AH); 8.11 (d, 1H) 8.70 (d, AH); 13.4 (bs, 1H). The sample had 96% isolated yield.

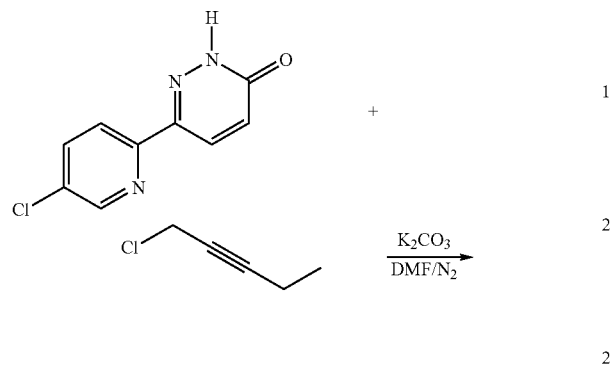

B.

To a 100 mL 3 neck flask equipped with magnetic stirrer, addition funnel, and nitrogen inlet was charged 150 milligrams (mg) of 6-(5-chloropyridin-2-yl)pyridazin-3(2H)-one (0.72 mmol), 200 mg of potassium carbonate (1.44 mmol), and 20 mL of dry DMF. The reaction mixture was stirred for about 30 minutes at ambient temperature followed by the dropwise addition of 82 mg of pentynyl chloride (0.8 mmol) in about 2 mL of dry DMF. The reaction was stirred overnight at ambient temperature, and checked by TLC and GC the next morning. No starting material remained, and one new product was formed. The reaction was poured into about 100 mL of water, and extracted with 3×50 mL of ethyl ether. The combined ether extract was washed with 100 mL of water, 100 mL of saturated aqueous sodium chloride solution, dried, and stripped to afford 175 mg of a tan solid The NMR data is as follows: 300 MHz $^1$H NMR (CDCl3, TMS=0 ppm) 1.15 (t, 3H); 2.20 (m, 2H); 4.95 (s, 2H); 7.05 (d, AH); 7.75 (d, AH); 8.15 (d, AH); 8.30 (d, AH); 8.50 (s, AH). The sample had 89% isolated yield and was >95% pure by GC.

Example 3

6-(5-chloropyridin-2-yl)-2-pent-2-ynylpyridazin-3(2H)-one

Compound 8, method II

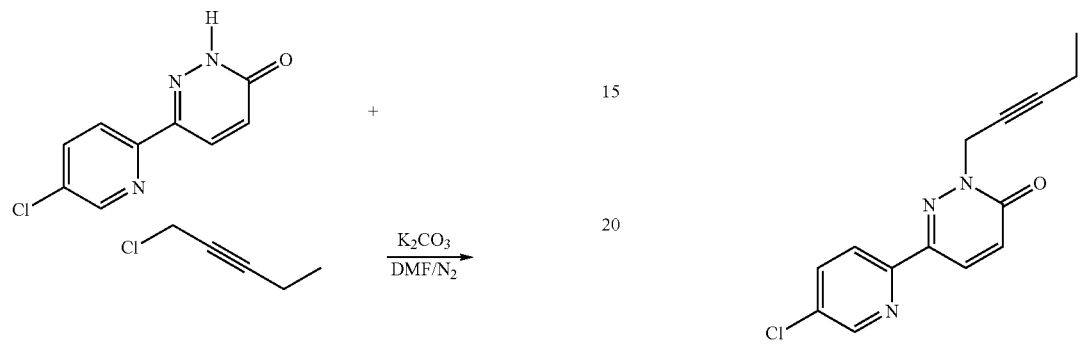

A. 2-Bromo-5-chloropyridine

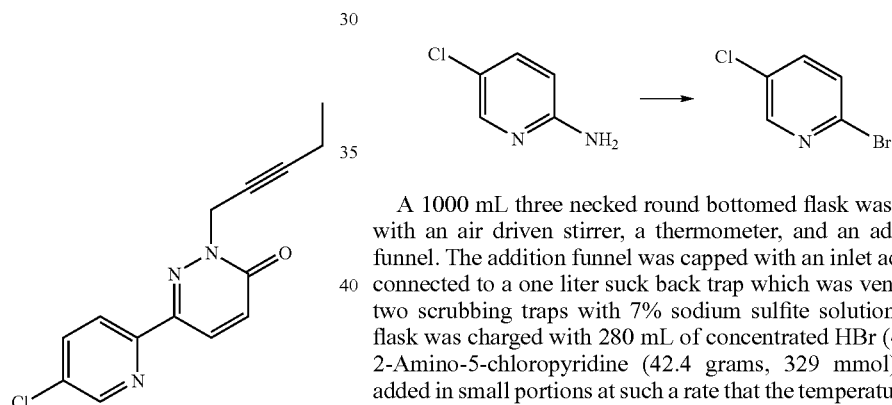

A 1000 mL three necked round bottomed flask was fitted with an air driven stirrer, a thermometer, and an addition funnel. The addition funnel was capped with an inlet adapter connected to a one liter suck back trap which was vented to two scrubbing traps with 7% sodium sulfite solution. The flask was charged with 280 mL of concentrated HBr (48%). 2-Amino-5-chloropyridine (42.4 grams, 329 mmol) was added in small portions at such a rate that the temperature did not exceed 28° C. An ice/salt bath was used to cool the reaction to 5° C. and bromine (45 ml, d=3.1, g/ml, 87 5 mmol) was added in portions such that the temperature did not exceed 10° C. After five minutes of stirring the temperature was cooled to 5° C. and a solution of sodium nitrite (56.8 grams, 820 mmol) in approximately 130 mL of water was added dropwise over 90 minutes at such a rate that the reaction temperature did not exceed 10° C. Out-gassing of bromine and nitrogen was noted during the addition. The reaction was allowed to stir for one hour at 5-10° C. Then 50% aqueous NaOH (d=1.52 g/ml, about 160 ml) was added drop wise over 90 minutes at such a rate that the reaction temperature did not exceed 10° C. The basic reaction slurry was extracted with 600 mL of ether (some non crystalline solid did not dissolve and was removed with the drying agent by filtration). The ether extract was cooled in an ice water bath and was washed with 200 mL of saturated sodium bisulfite solution until neutral to starch iodide paper. The organic extract was washed with 100 mL of saturated sodium chloride solution, dried with MgSO$_4$, and concentrated under reduced pressure to yield a volatile solid. The water bath was kept below 30° C. during the strip. The product can disappear if dried in a vacuum oven. The yield was 57.2 grams, and the purity was 95% by GC. The NMR data is as follows: 300 MHz $^1$H NMR (CDCl3, TMS=0 ppm) 7.20 (d, 1H); 7.80 (d, 1H); 8.45 (s, 1H).

B. 2-Acetyl-5-chloropyridine

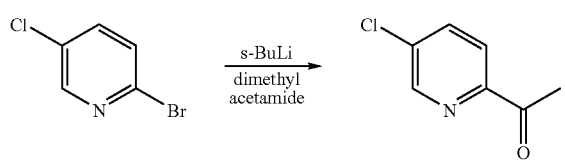

A two liter 4 neck flask was equipped with an overhead air-driven stirrer, a low temperature thermometer and a 250 mL addition funnel. The reaction setup was flushed with nitrogen overnight. A 1.3 M cyclohexane solution of s-butyl-lithium (222 ml, 0.289 mol) was charged to the addition funnel with a cannula. 2-Bromo-4-chloropyridine (57.72 g; 0.30 mol) and 600 mL of anhydrous ether were charged to the flask and then cooled in an acetone/dry ice bath. The temperature of the resultant slurry was −76° C. The s-butyllithium was added dropwise at a rate to maintain the temperature at −74° C. or lower. The addition took 1.5 hours. When the addition was complete the addition funnel was rinsed with 20 mL of anhydrous ether, then charged with 30.7 mL of dimethylacetamide (0.330 mol) and 30 mL of anhydrous ether. Ten minutes after the completion of the s-butyllithium addition, the dimethylacetamide solution was added dropwise to the reaction mixture, again maintaining the temperature at −74° C. or less. This addition took about 40 minutes. The reaction mixture was held at −76° C. for one hour after the dimethylacetamide addition was complete, then the bath was removed and the temperature allowed to warm to −30° C. At this temperature the cold bath was replaced and the reaction was quenched with 200 mL of 3 N HCl. The reaction mixture was allowed to warm to room temperature. The ether layer was separated, washed with water and saturated brine, dried over MgSO$_4$ and concentrated under reduced pressure. The residue was dissolved in methylene chloride, slurried with one weight equivalent of silica gel, filtered through celite and concentrated under reduced pressure. The resultant solid was an orange color. The product was recrystallized from hexane to give 29.35 g of product as an orange/tan solid. The NMR data is as follows: 300 MHz $^1$H NMR (CDCl3, TMS=0 ppm) 2.70 (s, 3H); 7.85 (d, 1H); 7.95 (d, 1H); 8.63 (s, 1H).

C. 6-(5-chloro-2-pyridyl)-pyridazin-3-one

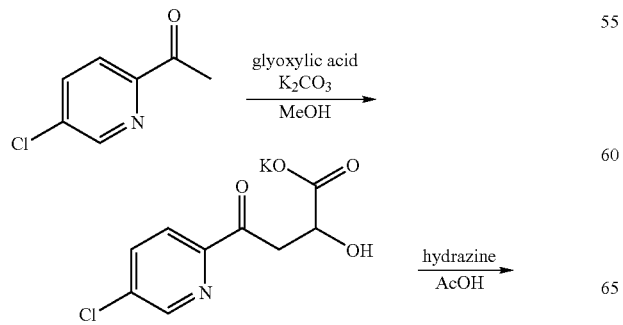

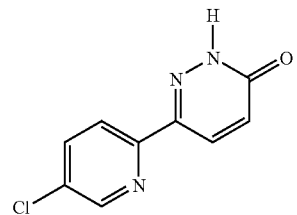

To a slurry of 5.05 g of 2-acetyl-5-chloropyridine (32.4 mmol) in 36 mL of methanol at room temperature was added 60 mL of water and 4.8 g of 50% glyoxylic acid (32.4 mmol). Potassium carbonate (8.96 g, 2 equivalents) was added carefully (foaming), and the reaction mixture was stirred overnight at room temperature under nitrogen. The next day, the slurry was partially stripped on the rotovap to remove methanol (maximum bath temperature 30° C.). The slurry was transferred to a separatory funnel and extracted twice with methylene chloride. The aqueous phase was transferred back to a round bottom flask and treated carefully with 13.7 mL of acetic acid (foaming) followed by 1.9 g of hydrazine hydrate (38 mmol). The reaction mixture was refluxed for 2 hours. It became very dark. While cooling, potassium carbonate was carefully added until the pH was 7. The reaction mixture was cooled to room temperature, then filtered and washed with water. The solids were dried in a vacuum oven at 50° C. The product was 4.13 g of a fine black solid. The NMR data is as follows: 300 MHz $^1$H NMR (DMSO d-6, TMS=0 ppm) 7.10 (d, 1H); 7.75 (d, 1H); 8.11 (d, 1H) 8.70 (d, 1H); 13.4 (bs, 1H). The yield of pyridazinone was 61%.

D. 6-(5-chloropyridin-2-yl)-2-pent-2-ynylpyridazin-3(2H)-one

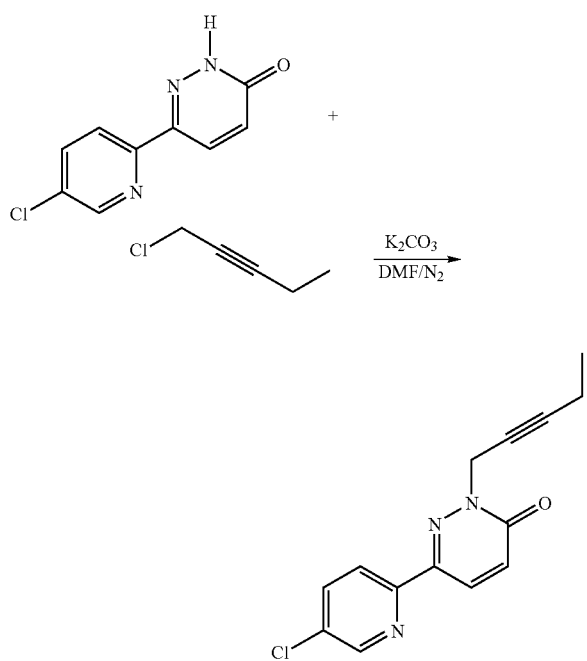

As in Example 2B.

Example 4

6-(5-chloropyridin-2-yl)-2-[4-(pentyloxy)but-2-ynyl]pyridazin-3(2H)-one

Compound 9

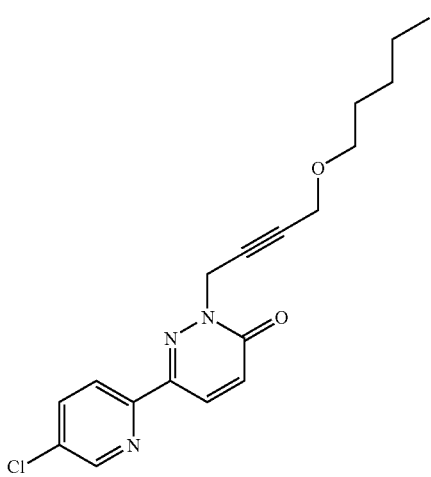 [SMILES: CCCCCOCC#CCn1nc(-c2ccc(Cl)cn2)ccc1=O]

A. 3-(pentyloxy)prop-1-yne

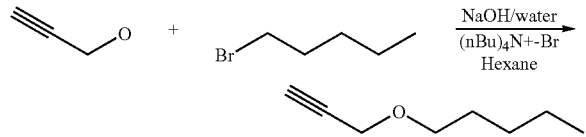

To a 500 mL 3 neck flask equipped with magnetic stirrer, addition funnel, and thermometer was charged 140 grams (g) of 50% sodium hydroxide in water (1.75 mol), 1.88 g of tetrabutyl ammonium bromide (5.83 mmol), and 120 mL of dry hexane. The reaction mixture was stirred rapidly at ambient temperature followed by the dropwise addition of 13 g (0.232 moles) of propargyl alcohol and 43.16 ml (0.35 moles) of n-pentyl bromide. The reaction was refluxed for 3 hours, after which two phases formed when agitation was stopped. The upper (organic) phase was collected via a separatory funnel, and this material was distilled at atmospheric pressure. The purest fractions were combined to afford 28.2 g of a clear pale yellow liquid which was consistent with the target molecule upon analysis by $^1$H NMR. The NMR data is as follows: 300 MHz $^1$H NMR (CDCl3, TMS=0 ppm) 0.95 (m, 3H); 1.33 (m, 4H); 1.55 (m, 2H); 2.40 (s, 1H); 3.50 (m, 2H); 4.15 (s, 2H).

B. 4-(pentyloxy)but-2-yn-1-ol

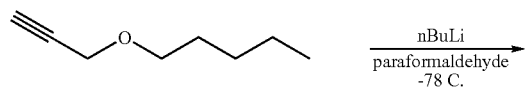

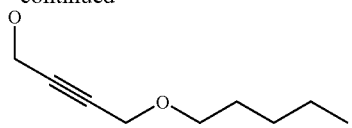

To a 500 mL 3 neck flask equipped with magnetic stirrer, addition funnel, and nitrogen inlet was charged 10 grams (g) of 3-(pentyloxy)prop-1-yne (0.72 mmol), and 140 mL of dry ethyl ether. The reaction mixture was cooled to −78° C. with stirring followed by the dropwise addition of 37.5 mls (60 mmole) of 1.6M n-Butyl lithium solution in hexane. The temperature was adjusted to 0° C. and 5.4 g (180 mmole) of solid paraformaldehyde was added. The mixture was then stirred at ambient temperature overnight. Ether and water was added to the mixture and the ether layer was separated, washed with water and brine, dried over anhydrous magnesium sulfate and concentrated under vacuum on a rotary evaporator. Isolated 9.44 g of a colorless liquid which was consistent with the desired structure upon analysis by 300 MHz $^1$H NMR.

The NMR Data is as follows: 300 MHz $^1$H NMR (CDCl3, TMS=0 ppm) 0.95 (m, 3H); 1.35 (m, 4H); 1.60 (m, 2H); 2.6 (bs, 1H); 3.50 (m, 4H); 4.15 (s, 2H).

C. 4-(pentyloxy)but-2-ynyl methanesulfonate

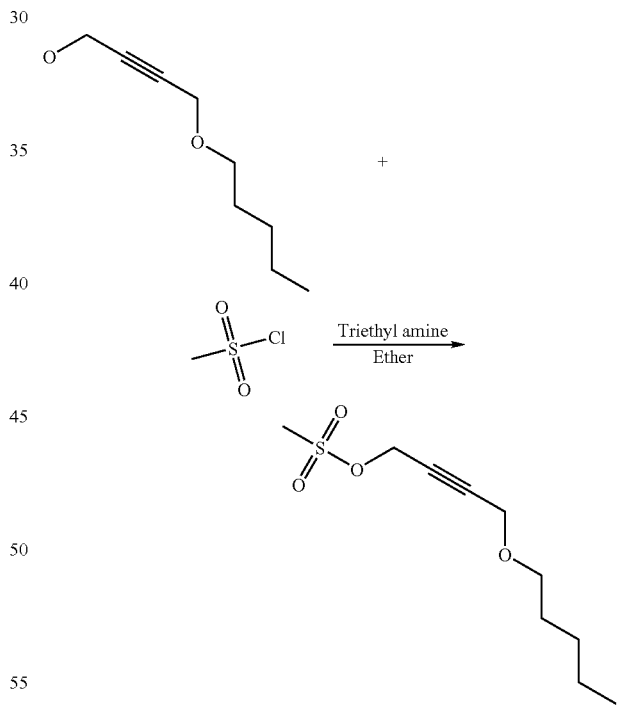

To a 300 mL 3 neck flask equipped with magnetic stirrer, addition funnel, and nitrogen inlet was charged 7.42 grams (g) of 4-(pentyloxy)but-2-yn-1-ol (0.45 mmol), 70 mL of dry ethyl ether, and 6.8 g (68 mmoles) of anhydrous triethyl amine The reaction mixture was cooled to 5° C. with stirring followed by the dropwise addition of 4.95 g (43 mmoles) of methane sulfonyl chloride in 7 mls of ethyl ether. The temperature was adjusted to 0° C. and 5.4 g (180 mmole) of solid paraformaldehyde was added. The mixture was then stirred at 10-15° C. for 6 hours, then diluted with another 40 mls of ether and 70 mls of water. The organic phase was separated, and washed with water and brine, then dried over anhydrous magnesium sulfate. Filtered and concentrated under vacuum on a rotary evaporator. Isolated 9.5 g of a clear colorless liquid which was consistent with the desired structure upon analysis by 300 MHz $^1$H NMR.

The NMR data is as follows: 300 MHz $^1$H NMR (CDCl3, TMS=0 ppm) 0.90 (m, 3H); 1.35 (m, 4H); 1.55 (m, 2H); 3.15 (s, 3H); 3.50 (m, 2H); 4.20 (s, 2H); 4.90 (s, 2H).

D. 6-(5-chloropyridin-2-yl)-2-[4-(pentyloxy)but-2-ynyl]pyridazin-3(2H)-one

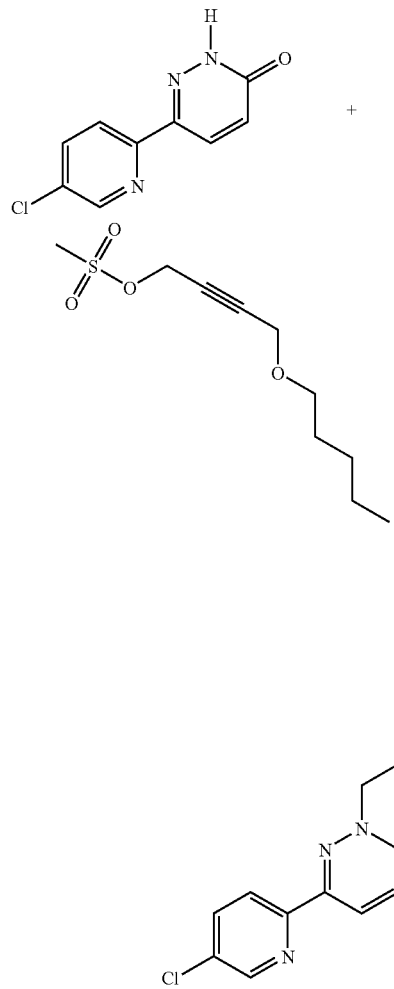

To a 100 mL 3 neck flask equipped with magnetic stirrer, addition funnel, and nitrogen inlet was charged 2.13 grams (g) of 6-(5-chloropyridin-2-yl)pyridazin-3(2H)-one (10.3 mmol), 2.20 g of potassium carbonate (16 mmol), and 50 mL of dry DMF. The reaction mixture was stirred for about 30 minutes at ambient temperature followed by the dropwise addition of 2.54 g of 4-(pentyloxy)but-2-ynyl methanesulfonate (10.8 mmol) in about 5 mL of dry DMF. The reaction was stirred overnight at ambient temperature, and checked by TLC and GC the next morning. No starting material remained, and one new product was formed. The reaction was poured into about 100 mL of water, and extracted with 3×50 mL of ethyl ether. The combined ether extract was washed with 100 mL of water, 100 mL of saturated aqueous sodium chloride solution, dried, and stripped to the crude product which was purified by silica gel column chromatography. The pure fractions were combined and concentrated under vacuum on a rotary evaporator to afford 1.3 g of a white solid. The NMR data is as follows: 300 MHz $^1$H NMR (CDCl3, TMS=0 ppm) 0.90 (m 3H); 1.30 (m, 4H); 1.55 (m, 2H); 3.45 (t, 2H); 4.15 (s, 2H); 5.05 (s, 2H); 7.05 (d, 1H); 7.75 (d, 1H); 8.15 (d, 1H); 8.30 (d, 1H); 8.55 (s, 1H).

Example 5

6-(5-bromopyrimidin-2-yl)-2-dec-2-ynylpyridazin-3(2H)-one

Compound 34

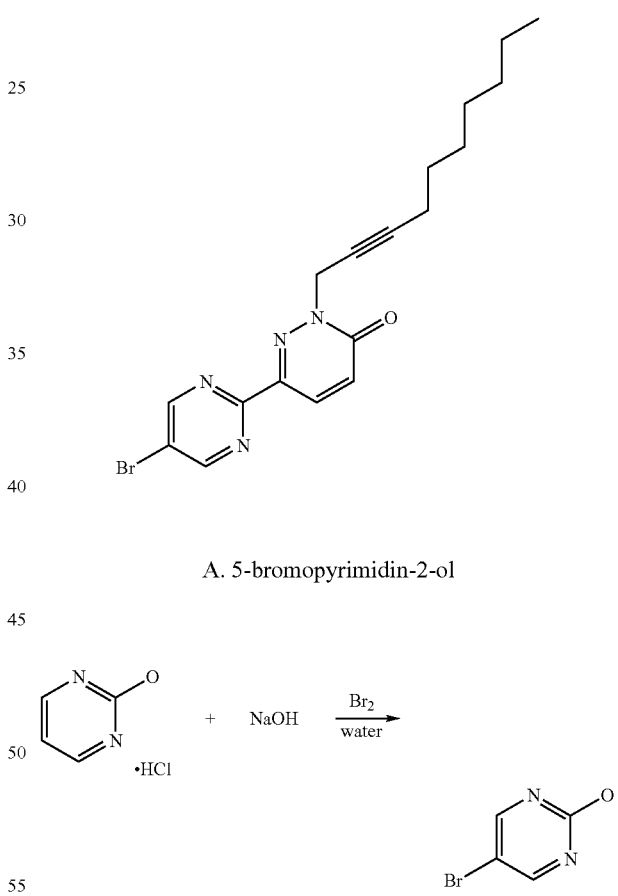

A. 5-bromopyrimidin-2-ol

To a 500 mL 3 neck flask equipped with magnetic stirrer, addition funnel, and thermometer was charged 6.63 grams (g) of pyrimidin-2-ol hydrochloride (50 mmol), and 250 mL of water. Then 8.33 ml (50 mmol) of 6M aqueous NaOH was added, followed by the dropwise addition of 9.0 g (56 mmol) of bromine over 15 minutes. The reaction was stirred for about 30 minutes at ambient temperature. Added a few drops of sodium bisulfite solution to discharge the residual bromine, then stripped to dryness. Dissolved the residue in hot ethanol, filtered, and stripped to afford 5.75 g of a solid which was consistent with the title compound upon analysis by NMR. The NMR data is as follows: 300 MHz ¹H NMR (DMSO-d6, TMS=0 ppm) 8.45 (s 2H);

B. 5-bromo-2-chloropyrimidine

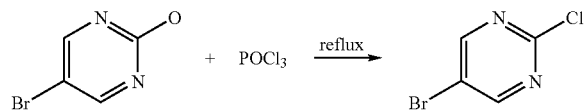

To a 100 mL 1 neck flask equipped with magnetic stirrer, reflux condenser and thermometer was charged 5.75 grams (g) of 5-bromopyrimidin-2-ol (32.8 mmol), and 50 mL of phosphorus oxychloride. The solution was heated at reflux for 2 hours, cooled, and concentrated under vacuum on a rotary evaporator. Isolated 6.3 g of a white solid which was consistent with the title compound upon analysis by NMR. The NMR data is as follows: 300 MHz ¹H NMR (CDCl3, TMS=0 ppm) 8.70 (s 2H);

C. 5-bromo-2-chloropyrimidine

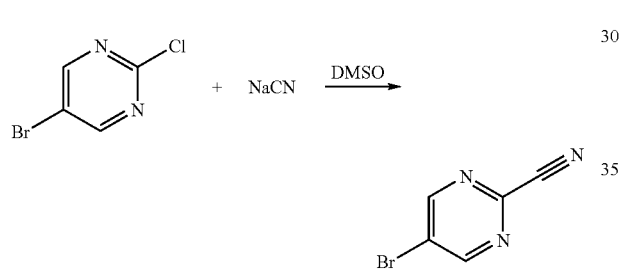

To a 50 mL 1 neck flask equipped with magnetic stirrer, nitrogen inlet and thermometer was charged 3.16 grams (g) of 5-bromo-2-chloropyrimidine (16.3 mmol), and 20 mL of anhydrous dimethylsulfoxide. The solution was cooled to ~5° C. (began to freeze), and the sodium cyanide (0.8 g 16.3 mmol) was added in one portion. Allowed to slowly warm to room temperature, and stirred for another 3 hours. Then the solution was poured into ~100 ml of water and extracted with ethyl acetate. The organic extract was washed with brine, dried over anhydrous magnesium sulfate, filtered, and concentrated under vacuum on a rotary evaporator. Silica gel column chromatography (ethyl acetate/hexane) afforded 0.85 g of a white solid which was consistent with the title compound upon analysis by NMR. The NMR data is as follows: 300 MHz ¹H NMR (CDCl3, TMS=0 ppm) 8.95 (s 2H);

D. 1-(5-bromopyrimidin-2-yl)ethanone

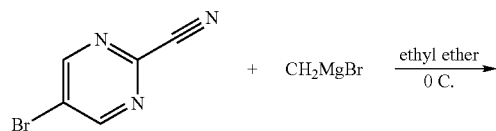

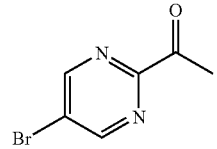

To a 50 mL 1 neck flask equipped with magnetic stirrer, nitrogen inlet and thermometer was charged 0.68 grams (g) of 5-Bromo-pyrimidine-2-carbonitrile (3.7 mmol), and 20 mL of anhydrous ether. The solution was cooled to ~0° C., and the methyl magnesium bromide solution 3.0M in ether; 1.1 ml, 3.3 mmol) was added dropwise. Allowed to slowly warm to room temperature, and quenched with aqueous ammonium chloride solution. Extracted with 3×50 mls of ether and washed with brine. Dried over anhydrous magnesium sulfate, and concentrated under vacuum on a rotary evaporator. The crude product thus obtained was chromatographed on silica gel with ethyl acetate and hexane. afforded 0.22 g of a white solid which was consistent with the title compound upon analysis by NMR. The NMR data is as follows: 300 MHz ¹H NMR (CDCl3, TMS=0 ppm) 2.75 (s, 3H); 9.00 (s 2H).

E. 6-(5-bromopyrimidin-2-yl)pyridazin-3(2H)-one

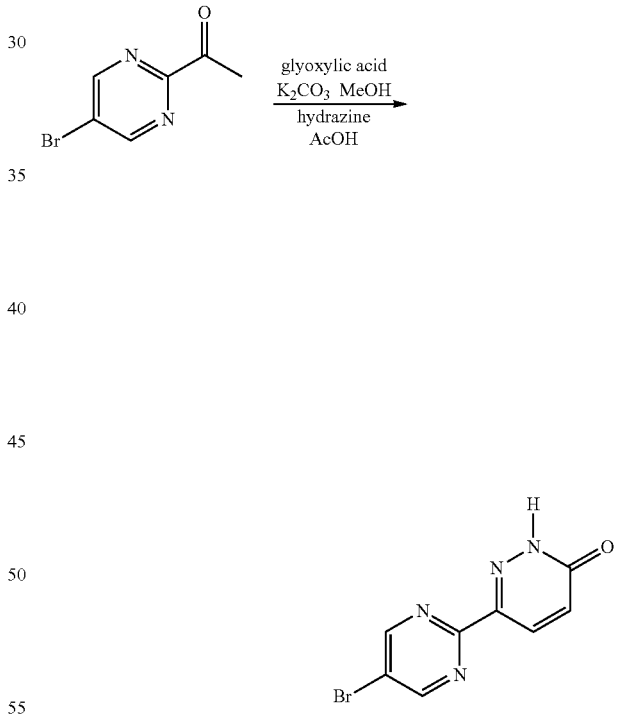

To a 50 mL 1 neck flask equipped with magnetic stirrer, nitrogen inlet and thermometer was charged 0.22 grams (g) of 1-(5-bromopyrimidin-2-yl)ethanone (1.09 mmol), 0.17 g (1.1 mmol) glyoxylic acid, and 2.5 mL of methanol and 2.5 mls of water. To this solution was added 0.3 g (2.2 mmol) of potassium carbonate. The reaction was stirred overnight at room temperature. Methanol was then concentrated under vacuum on a rotary evaporator, and the resulting aqueous solution was washed twice with 5 mls of methylene chloride. To the aqueous solution was then added 0.6 mls of acetic acid and 0.07 g (1.4 mmol) of hydrazine monohydrate. This solution was refluxed for 2 hours, then cooled at 5° C. The resulting solid was collected by vacuum filtration to afford 30 mg of a brown solid which was consistent with the target compound upon analysis by NMR. The NMR data is as follows: 300 MHz $^1$H NMR (CDCl3, TMS=0 ppm) 2.75 (s, 3H); 9.00 (s, 2H).

F. 6-(5-bromopyrimidin-2-yl)-2-dec-2-ynylpyridazin-3(2H)-one

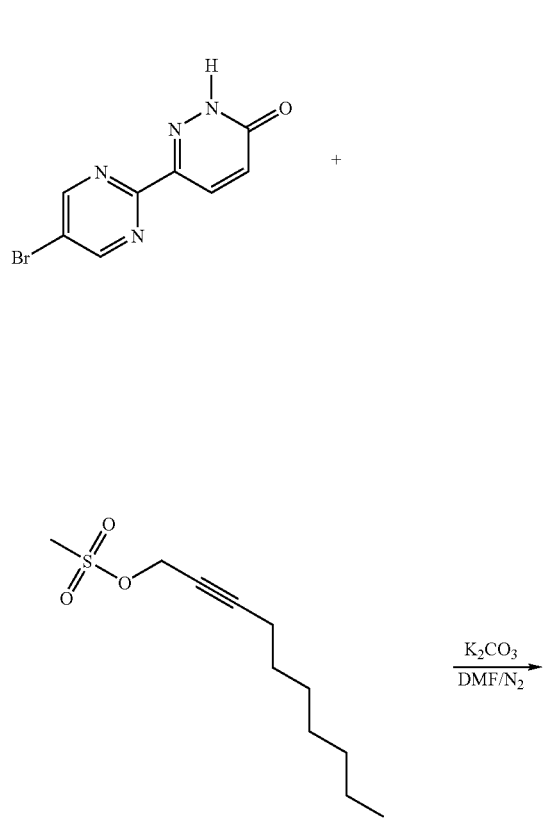

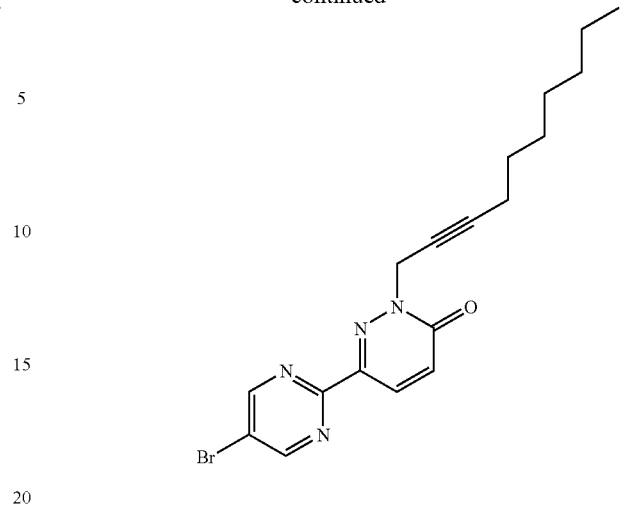

To a 20 mL 1 neck flask equipped with magnetic stirrer, and nitrogen inlet was charged 30 milligrams (mg) of 6-(5-bromopyrimidin-2-yl)pyridazin-3(2H)-one (0.12 mmol), 33 mg of potassium carbonate (0.24 mmol), and 5 mL of dry DMF. The reaction mixture was stirred for about 30 minutes at ambient temperature followed by the addition of 100 mg of dec-2-ynyl methanesulfonate (0.43 mmol) in one portion. The reaction was stirred overnight at ambient temperature. The reaction was poured into about 10 mL of water, and extracted with 3×10 mL of ethyl acetate. The combined organic extract was washed with 10 mL of water, 10 mL of saturated aqueous sodium chloride solution, dried, and stripped to the crude product which was purified by silica gel column chromatography (20% ethyl acetate/80% hexanes). The pure fractions were combined and concentrated under vacuum on a rotary evaporator to afford 6 g of a white solid consistent with the title compound upon analysis by NMR. The NMR data is as follows: 300 MHz $^1$H NMR (CDCl3, TMS=0 ppm) 0.85 (m 3H); 1.25 (m, 6H); 1.60-1.65 (m, 4H); 2.15 (m, 2H); 5.05 (s, 2H); 7.05 (d, 1H); 8.35 (d, 1H); 9.00 (s, 2H).

| Compound | STRUCTURE | Method of preparation | Proton NMR |
|---|---|---|---|
| 1 | 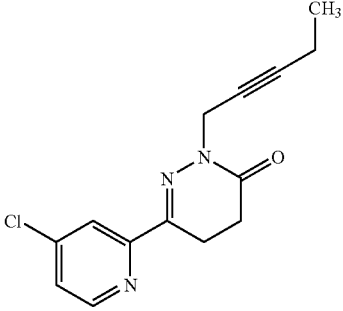 [SMILES: CCC#CCN1N=C(c2cc(Cl)ccn2)CCC1=O] | As in example 1 | 300 MHz $^1$H NMR (CDCl3, TMS = 0 ppm) 1.20 (t, 3 H); 2.20 (m, 2 H); 2.65 (t, 2 H); 3.30 (t, 2 h); 4.70 (s, 2 H); 7.30 (m, 1 H); 8.20 (s, 1 H); 8.50 (s, 1 H) |

| Compound | STRUCTURE | Method of preparation | Proton NMR |
|---|---|---|---|
| 2 | (6-chloropyridin-2-yl pyridazinone with pent-2-ynyl group) | As in example 1 | 300 MHz ¹H NMR (CDCl3, TMS = 0 ppm) 1.15 (t, 3 H); 2.25 (m, 2 H); 2.60 (t, 2 H); 3.25 (t, 2 H); 4.70 (s, 2 H); 7.30 (d, 1 H); 7.75 (t, 1 H); 8.15 (d, 1 H); |
| 3 | (5-chloropyridin-2-yl pyridazinone with pent-2-ynyl group) | Example 1 | 300 MHz ¹H NMR (CDCl3, TMS = 0 ppm) 1.15 (t, 3 H); 2.20 (m, 2 H); 2.60 (t, 2 H); 3.25 (t, 2 H); 4.70 (s, 2 H); 7.75 (d, 1 H); 8.15 (d, 1 H); 8.50 (s, 1 H). |
| 4 | (5,6-dichloropyridin-2-yl pyridazinone with pent-2-ynyl group) | As in example 1 | 300 MHz ¹H NMR (CDCl3, TMS = 0 ppm) 1.10 (t, 3 H); 2.20 (m, 2 H); 2.60 (t, 2 H); 3.20 (t, 2 H); 4.65 (s, 2 H); 7.80 (d, 1 H); 8.10 (d, 1 H) |
| 5 | (3-chloropyridin-2-yl pyridazinone with pent-2-ynyl group) | As in example 1 | 300 MHz ¹H NMR (CDCl3, TMS = 0 ppm) 1.10 (t, 3 H); 2.15 (m, 2 H); 2.60 (t, 2 H); 3.15 (t, 2 H); 4.60 (s, 2 H); 7.25 (m, 1 H); 7.85 (d, 1 H); 8.55 (m, 1 H) |
| 6 | (3,5-dichloropyridin-2-yl pyridazinone with pent-2-ynyl group) | As in example 1 | 300 MHz ¹H NMR (CDCl3, TMS = 0 ppm) 1.10 (t, 3 H); 2.15 (m, 2 H); 2.60 (t, 2 H); 3.15 (t, 2 H); 4.60 (s, 2 H); 7.85 (s, 1 H); 8.50 (s, 1 H) |
| 7 | (3,5,6-trichloropyridin-2-yl pyridazinone with pent-2-ynyl group) | As in example 1 | 300 MHz ¹H NMR (CDCl3, TMS = 0 ppm) 1.10 (t, 3 H); 2.15 (m, 2 H); 2.60 (t, 2 H); 3.15 (t, 2 H); 4.60 (s, 2 H); 7.90 (s, 1 H) |

-continued

| Compound | STRUCTURE | Method of preparation | Proton NMR |
|---|---|---|---|
| 8 | 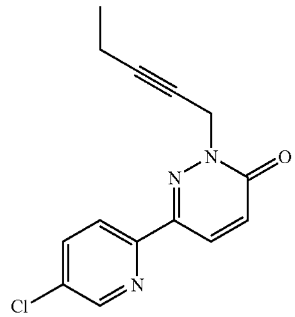 [SMILES: CCC#CCn1nc(-c2ccc(Cl)cn2)ccc1=O] | Example 3 | 300 MHz ¹H NMR (CDCl3, TMS = 0 ppm) 1.15 (t, 3 H); 2.20 (m, 2 H); 4.95 (s, 2 H); 7.05 (d, 1 H); 7.75 (d, 1 H); 8.15 (d, 1 H); 8.30 (d, 1 H); 8.50 (s, 1 H). |
| 9 | 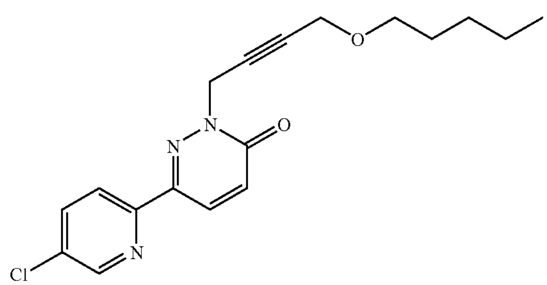 [SMILES: CCCCCOCC#CCn1nc(-c2ccc(Cl)cn2)ccc1=O] | Example 4 | 300 MHz ¹H NMR (CDCl3, TMS = 0 ppm) 0.90 (m 3 H); 1.30 (m, 4 H); 1.55 (m, 2 H); 3.45 (t, 2 H); 4.15 (s, 2 H); 5.05 (s, 2 H); 7.05 (d, 1 H); 7.75 (d, 1 H); 8.15 (d, 1 H); 8.30 (d, 1 H); 8.55 (s, 1 H). |
| 10 | 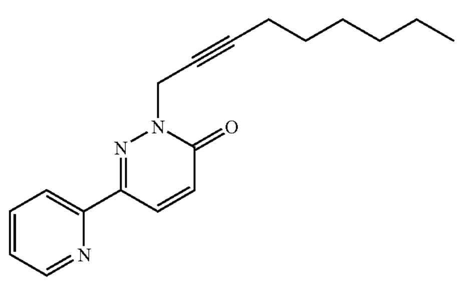 [SMILES: CCCCCCC#CCn1nc(-c2ccccn2)ccc1=O] | As in example 3 | 300 MHz ¹H NMR (CDCl3, TMS = 0 ppm) 0.85 (m 3 H); 1.20-1.60 (m, 8 H); 2.25 (m, 2 H); 5.05 (s, 2 H); 7.05 (d, 1 H); 7.30 (m, 1 H); 7.75 (t, 1 H); 8.20 (d, 1 H); 8.40 (d, 1 H); 8.70 (d, 1 H). |
| 11 | 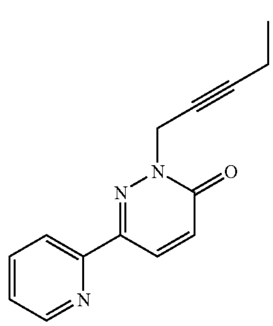 [SMILES: CCC#CCn1nc(-c2ccccn2)ccc1=O] | As in example 3 | 300 MHz ¹H NMR (CDCl3, TMS = 0 ppm) 1.10 (t, 3 H); 2.20 (m, 2 H); 4.95 (s, 2 H); 7.05 (d, 1 H); 7.30 (m, 1 H); 7.75 (t, 1 H); 8.20 (d, 1 H); 8.40 (d, 1 H); 8.70 (d, 1 H). |

-continued
| Compound | STRUCTURE | Method of preparation | Proton NMR |
|---|---|---|---|
| 12 | 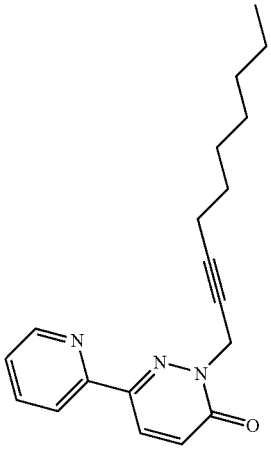 [SMILES: CCCCCCCC#CCn1nc(-c2ccccn2)ccc1=O] | As in example 3 | 300 MHz ¹H NMR (CDCl3, TMS = 0 ppm) 0.85 (m 3 H); 1.15-1.60 (m, 10 H); 2.25 (m, 2 H); 5.05 (s, 2 H); 7.05 (d, 1 H); 7.30 (m, 1 H); 7.80 (t, 1 H); 8.20 (d, 1 H); 8.40 (d, 1 H); 8.65 (d, 1 H). |
| 13 | 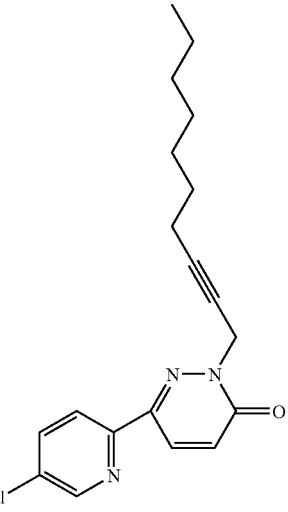 | As in example 3 | 300 MHz ¹H NMR (CDCl3, TMS = 0 ppm) 0.90 (m 3 H); 1.15-1.70 (m, 10 H); 2.20 (m, 2 H); 5.05 (s, 2 H); 7.05 (d, 1 H); 7.80 (t, 1 H); 8.20 (d, 1 H); 8.40 (d, 1 H); 8.60 (s, 1 H). |
| 14 | 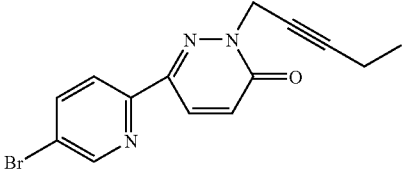 [SMILES: CCC#CCn1nc(-c2ccc(Br)cn2)ccc1=O] | As in example 3 | 300 MHz ¹H NMR (CDCl3, TMS = 0 ppm) 1.15 (t, 3 H); 2.20 (m, 2 H); 4.95 (s, 2 H); 7.05 (d, 1 H); 7.80 (d, 1 H); 8.15 (d, 1 H); 8.35 (d, 1 H); 8.60 (s, 1 H). |
| 15 | 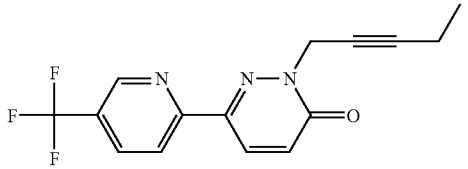 [SMILES: CCC#CCn1nc(-c2ccc(C(F)(F)F)cn2)ccc1=O] | As in example 3 | 300 MHz ¹H NMR (CDCl3, TMS = 0 ppm) 1.15 (t, 3 H); 2.20 (m, 2 H); 5.00 (s, 2 H); 7.10 (d, 1 H); 8.10 (d, 1 H); 8.35 (m 2 H); 8.90 (s, 1 H) |
| 16 | 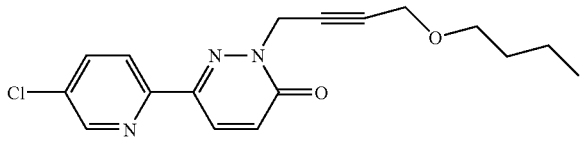 [SMILES: CCCCOCC#CCn1nc(-c2ccc(Cl)cn2)ccc1=O] | As in example 4 | 300 MHz ¹H NMR (CDCl3, TMS = 0 ppm) 0.90 (t 3 H); 1.35 (m, 2 H); 1.55 (m, 2 H); 3.45 (t, 2 H); 4.15 (s, 2 H); 5.05 (s, 2 H); 7.05 (d, 1 H); 7.75 (d, 1 H); 8.15 (d, 1 H); 8.30 (d, 1 H); 8.55 (s, 1 H). |

| Compound | STRUCTURE | Method of preparation | Proton NMR |
|---|---|---|---|
| 17 | 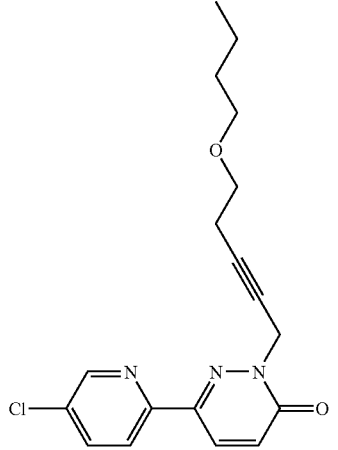 [SMILES: CCCCOCCC#CCn1nc(-c2ccc(Cl)cn2)ccc1=O] | As in example 4 | 300 MHz $^1$H NMR (CDCl3, TMS = 0 ppm) 0.90 (t 3 H); 1.35 (m, 2 H); 1.55 (m, 2 H); 3.45 (t, 2 H); 3.55 (t, 2 H); 5.00 (s, 2 H); 7.05 (d, 1 H); 7.75 (d, 1 H); 8.15 (d, 1 H); 8.30 (d, 1 H); 8.55 (s, 1 H). |
| 18 | 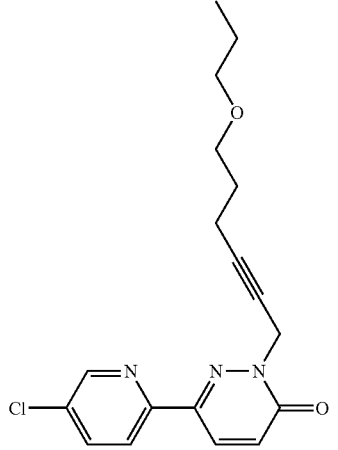 [SMILES: CCCOCCCC#CCn1nc(-c2ccc(Cl)cn2)ccc1=O] | As in example 4 | 300 MHz $^1$H NMR (CDCl3, TMS = 0 ppm) 0.90 (t 3 H); 1.55 (m, 2 H); 1.75 (m, 2 H); 2.30 (m, 2 H); 3.35 (t, 2 H); 3.50 (t, 2 H); 5.00 (s, 2 H); 7.05 (d, 1 H); 7.75 (d, 1 H); 8.15 (d, 1 H); 8.30 (d, 1 H); 8.55 (s, 1 H). |
| 19 | 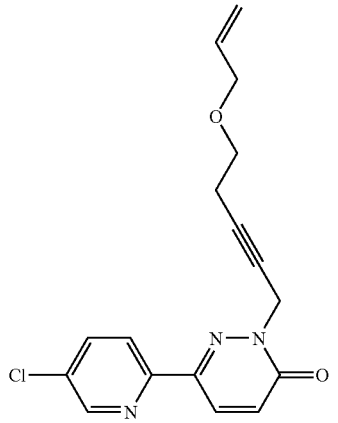 [SMILES: C=CCOCCC#CCn1nc(-c2ccc(Cl)cn2)ccc1=O] | As in example 4 | 300 MHz $^1$H NMR (CDCl3, TMS = 0 ppm) 2.50 (m 2 H); 3.55 (t, 2 H); 4.00 (d, 2 H); 5.10 (s, 2 H); 5.15 (dd, 2 H); 5.90 (m, 1 H); 7.05 (d, 1 H); 7.75 (d, 1 H); 8.15 (d, 1 H); 8.30 (d, 1 H); 8.55 (s, 1 H). |

| Compound | STRUCTURE | Method of preparation | Proton NMR |
|---|---|---|---|
| 20 | 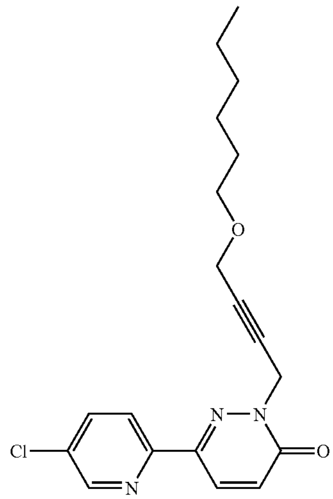 [SMILES: CCCCCCOCC#CCn1nc(-c2ccc(Cl)cn2)ccc1=O] | As in example 4 | 300 MHz ¹H NMR (CDCl3, TMS = 0 ppm) 0.85 (t 3 H); 1.30 (m, 6 H); 1.56 (m, 4 H); 3.45 (t, 2 H); 4.15 (s, 2 H); 5.05 (s, 2 H); 7.05 (d, 1 H); 7.70 (d, 1 H); 8.15 (d, 1 H); 8.30 (d, 1 H); 8.55 (s, 1 H). |
| 21 | 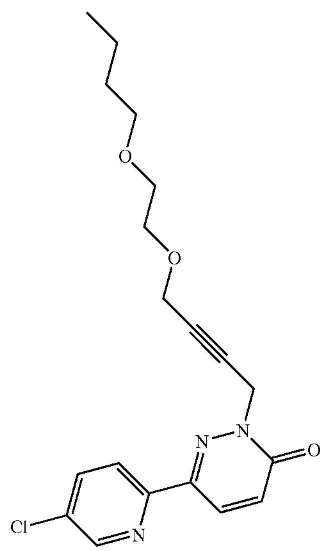 [SMILES: CCCCOCCOCC#CCn1nc(-c2ccc(Cl)cn2)ccc1=O] | As in example 4 | 300 MHz ¹H NMR (CDCl3, TMS = 0 ppm) 0.90 (t 3 H); 1.35 (m, 2 H); 1.56 (m, 2 H); 3.45 (t, 2 H); 3.60 (m, 2 H); 3.65 (m, 2 H); 4.25 (s, 2 H); 5.05 (s, 2 H); 7.00 (d, 1 H); 7.75 (d, 1 H); 8.10 (d, 1 H); 8.30 (d, 1 H); 8.55 (s, 1 H). |
| 22 | 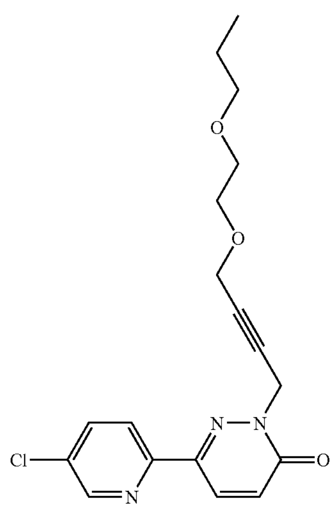 [SMILES: CCCOCCOCC#CCn1nc(-c2ccc(Cl)cn2)ccc1=O] | As in example 4 | 300 MHz ¹H NMR (CDCl3, TMS = 0 ppm) 0.90 (t 3 H); 1.60 (m, 2 H); 3.45 (t, 2 H); 3.60 (m, 2 H); 3.65 (m, 2 H); 4.25 (s, 2 H); 5.05 (s, 2 H); 7.05 (d, 1 H); 7.75 (d, 1 H); 8.15 (d, 1 H); 8.30 (d, 1 H); 8.55 (s, 1 H). |

-continued
| Compound | STRUCTURE | Method of preparation | Proton NMR |
|---|---|---|---|
| 23 | 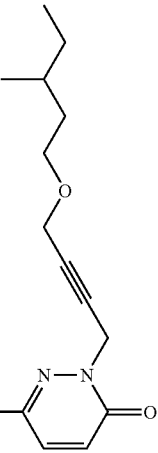 | As in example 4 | 300 MHz $^1$H NMR (CDCl3, TMS = 0 ppm) 0.85 (m 6 H); 1.10 (m, 1 H); 1.40 (m, 3 H); 1.70 (m, 1 H); 3.55 (m, 2 H); 4.15 (s, 2 H); 5.05 (s, 2 H); 7.05 (d, 1 H); 7.75 (d, 1 H); 8.15 (d, 1 H); 8.30 (d, 1 H); 8.55 (s, 1 H). |
| 24 | 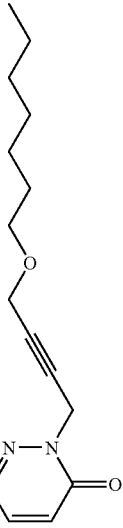 | As in example 4 | 300 MHz $^1$H NMR (CDCl3, TMS = 0 ppm) 0.85 (t 3 H); 1.25 (m, 8 H); 1.55 (m, 2 H); 3.50 (t, 2 H); 4.15 (s, 2 H); 5.00 (s, 2 H); 7.05 (d, 1 H); 7.75 (d, 1 H); 8.15 (d, 1 H); 8.30 (d, 1 H); 8.55 (s, 1 H). |
| 25 | 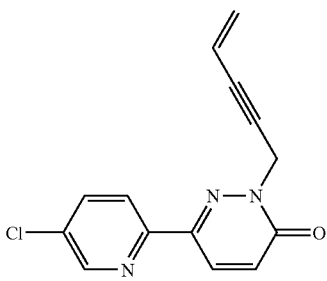 [SMILES: C=CC#CCn1nc(-c2ccc(Cl)cn2)ccc1=O] | As in example 3 | 300 MHz $^1$H NMR (CDCl3, TMS = 0 ppm) 5.10 (s, 2 H); 5.50 (d, 1 H); 5.70 (m, 2 H); 7.05 (d, 1 H); 7.75 (d, 1 H); 8.15 (d, 1 H); 8.35 (d, 1 H); 8.60 (s, 1 H). |
| 26 | 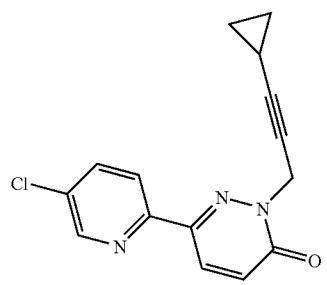 [SMILES: O=c1ccc(-c2ccc(Cl)cn2)nn1CC#CC1CC1] | As in example 3 | 300 MHz $^1$H NMR (CDCl3, TMS = 0 ppm) 0.70-0-76 (m, 4 H); 1.30 (m, 1 H); 4.95 (s, 2 H); 7.05 (d, 1 H); 7.80 (d, 1 H); 8.15 (d, 1 H); 8.30 (d, 1 H); 8.60 (s, 1 H). |

-continued

| Compound | STRUCTURE | Method of preparation | Proton NMR |
|---|---|---|---|
| 27 | (6-chloropyridin-2-yl pyridazinone with pent-2-ynyl group) | As in example 1 | 300 MHz ¹H NMR (CDCl3, TMS = 0 ppm) 1.10 (t, 3 H); 2.20 (m, 2 H); 4.95 (s, 2 H); 7.05 (d, 1 H); 7.30 (d, 1 H); 7.75 (m, 1 H); 8.15 (d, 1 H); 8.35 (d, 1 H) |
| 28 | (5,6-dichloropyridin-2-yl pyridazinone with pent-2-ynyl group) | As in example 2 | 300 MHz ¹H NMR (CDCl3, TMS = 0 ppm) 1.10 (t, 3 H); 2.20 (m, 2 H); 4.95 (s, 2 H); 7.05 (d, 1 H); 7.85 (d, 1 H); 8.15 (d, 1 H); 8.30 (d, 1 H) |
| 29 | (3-chloropyridin-2-yl pyridazinone with pent-2-ynyl group) | As in example 2 | 300 MHz ¹H NMR (CDCl3, TMS = 0 ppm) 1.10 (t, 3 H); 2.20 (m, 2 H); 4.95 (s, 2 H); 7.00 (d, 1 H); 7.35 (m, 1 H); 7.85 (m, 2 H); 8.60 (d, 1 H) |
| 30 | (3,5-dichloropyridin-2-yl pyridazinone with pent-2-ynyl group) | As in example 2 | 300 MHz ¹H NMR (CDCl3, TMS = 0 ppm) 1.10 (t, 3 H); 2.20 (m, 2 H); 4.95 (s, 2 H); 7.00 (d, 1 H); 7.85 (m, 2 H); 8.55 (s, 1 H) |
| 31 | (5-chloro-6-fluoropyridin-2-yl pyridazinone with pent-2-ynyl group) | As in example 2 | 300 MHz ¹H NMR (CDCl3, TMS = 0 ppm) 1.15 (t, 3 H); 2.20 (m, 2 H); 4.95 (s, 2 H); 7.00 (d, 1 H); 7.90 (t, 1 H); 8.10 (d, 1 H); 8.20 (d, 1 H) |
| 32 | (5,6-difluoropyridin-2-yl pyridazinone with pent-2-ynyl group) | As in example 2 | 300 MHz ¹H NMR (CDCl3, TMS = 0 ppm) 1.15 (t, 3 H); 2.20 (m, 2 H); 4.95 (s, 2 H); 7.00 (d, 1 H); 7.90 (t, 1 H); 8.10 (dd, 1 H); 8.20 (d, 1 H) |

| Compound | STRUCTURE | Method of preparation | Proton NMR |
|---|---|---|---|
| 33 | 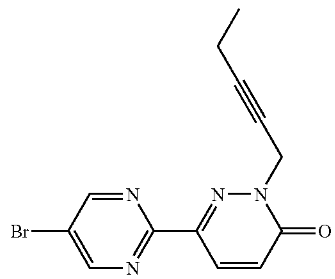 | As in example 5 | 300 MHz $^1$H NMR (CDCl3, TMS = 0 ppm) 1.10 (t, 3 H); 2.20 (m, 2 H); 5.05 (s, 2 H); 7.10 (d, 1 H); 8.35 (d, 1 H); 8.95 (s, 2 H). |
| 34 | 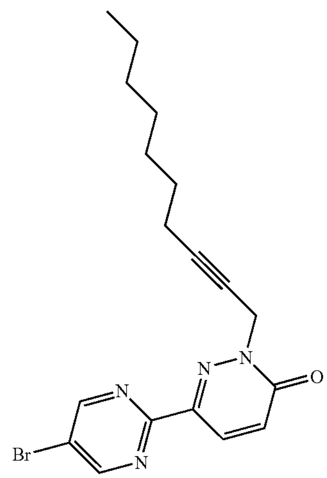 [SMILES: CCCCCCCC#CCn1nc(-c2ncc(Br)cn2)ccc1=O] | Example 5 | 300 MHz $^1$H NMR (CDCl3, TMS = 0 ppm) 0.85 (m 3 H); 1.25 (m, 6 H); 1.60-1.65 (m, 4 H); 2.15 (m, 2 H); 5.05 (s, 2 H); 7.05 (d, 1 H); 8.35 (d, 1 H); 9.00 (s, 2 H). |
| 35 | 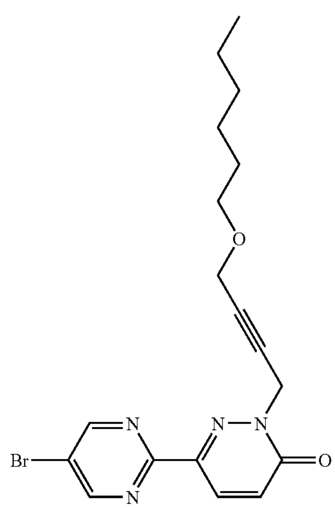 | As in example 5 | 300 MHz $^1$H NMR (CDCl3, TMS = 0 ppm) 0.85 (m 3 H); 1.30 (m, 4 H); 1.60-1.65 (m, 4 H); 3.45 (t, 2 H); 4.15 (s, 2 H); 5.15 (s, 2 H); 7.05 (d, 1 H); 8.35 (d, 1 H); 8.95 (s, 2 H). |

The following Practical Examples illustrate various aspects of the invention and should not be construed as limitations to the claims.

Practical Examples

Example 1

Inhibition of Δ-9 fatty acid desaturase

The following method was used to prepare microsomal Δ-9 fatty acid desaturase enzyme. Two 250 ml flasks containing 100 ml each of glucose-yeast extract medium (0.4% yeast extract and 2% glucose) were inoculated with *Saccharomyces cerevisiae* strain 12341 obtained from the American Type Culture Collection, and grown for 48 h at 30° C. with shaking at 250 rpm. The cells were used to inoculate a 4 liter flask containing 3.6 liters of medium. The cells were grown at 30° C. with gentle shaking at 90 rpm for 24 h. The cells were centrifuged at 2,500×G for 5 min. at 4° C., the cell pellet washed twice by suspension in ice-cold water and re-centrifugation, then re-suspended in an equal volume of cold 0.1 M potassium phosphate buffer, pH 7.2. The cells were lysed by homogenizing in a French press at an output pressure of 18,000 psi, and the homogenate was centrifuged at 8,000×G for 20 min. at 4° C. The supernatant was filtered through a plug of glass wool to remove the floating lipid layer and then centrifuged at 100,000×G for 90 min. at 4° C. and the resulting microsomal pellet suspended in 10 ml of ice-cold 0.1 M potassium phosphate buffer, pH 7.2, using a Dounce homogenizer to give a protein concentration of approximately 10 mg/ml. The preparation was frozen as aliquots in dry-ice/methanol and stored at −80° C.

Δ-9 Fatty acid desaturase assays were performed by measuring the desaturation of $^{14}$C-palmitoyl-CoA to $^{14}$C-palmitoleic acid using 0.5 ml reaction mixtures containing 0.1 M potassium phosphate buffer, pH 7.2, 1 mM NADH and 26 μM $^{14}$C-palmitoyl-CoA (0.028 μCi per assay) in 13×100 mm glass culture tubes. Compounds were added as 5 μl of solution in dimethylsulfoxide (DMSO), and tested at a series of twofold dilutions. The reagents were added to the culture tubes on ice, and the microsomal enzyme preparation (0.2 mg protein) added last. The tubes were incubated with vigorous shaking at 200 rpm at 30° C. for 5 min., then the reaction was stopped by adding 0.5 ml of 10% potassium hydroxide in methanol/water (90:10, v/v). The tubes were capped and saponified by heating at 80° C. for 30 min. 6 M HCl (0.5 ml) was added to each tube, followed by 0.5 ml of cyclohexane. The tubes were mixed vigorously and centrifuged briefly at 2,000 rpm to facilitate phase separation. The upper cyclohexane layer was removed and 100 μl analyzed by HPLC on a Supelcosil LC-18 column (25×4.6 mm) with methanol-water-phosphoric acid (90:9.9:0.1, by volume) as the mobile phase at a flow rate of 1 ml/min. A Packard A120 RAM detector was used to determine the amounts of radioactivity in the palmitic and palmitoleic acid fractions. The percent inhibition of desaturation was determined by comparing the production of palmitoleic acid in assays containing test compound with production in assays containing DMSO alone. The concentration of test compound which inhibited production of palmitoleic acid by 50% (I50) was determined from dose-response curves. I50 values for compounds are presented in Table 1.

TABLE 1

| Inhibition of Δ-9 fatty acid desaturase. | |
|---|---|
| Structure | I50 (μg/ml) |
| [structure] | 0.027 |
| [structure] | 0.033 |
| [structure] | <0.039 |

TABLE 1-continued

Inhibition of Δ-9 fatty acid desaturase.

| Structure | I50 (μg/ml) |
|---|---|
| 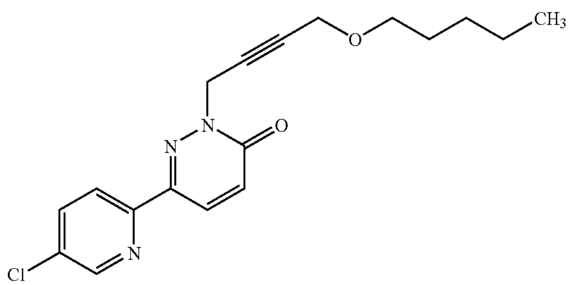 [SMILES: CCCCCOCC#CCn1nc(-c2ccc(Cl)cn2)ccc1=O] | 0.008 |
| 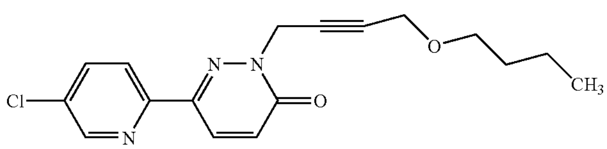 | 0.009 |
| 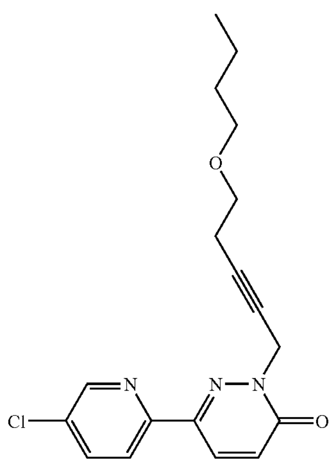 [SMILES: CCCCOCCC#CCn1nc(-c2ccc(Cl)cn2)ccc1=O] | 0.018 |
| 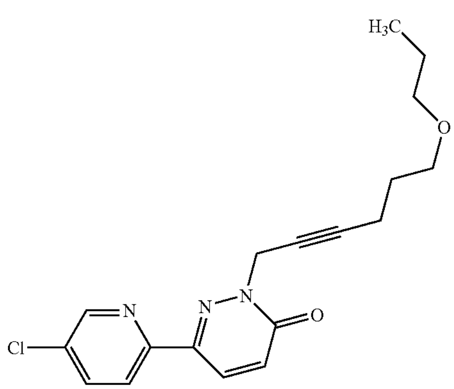 [SMILES: CCCOCCCC#CCn1nc(-c2ccc(Cl)cn2)ccc1=O] | 0.01 |
| 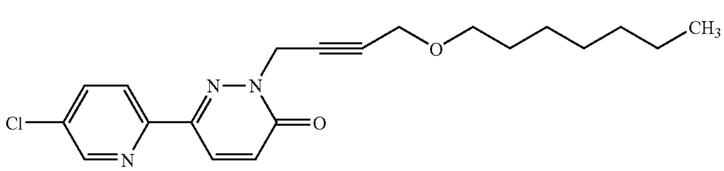 [SMILES: CCCCCCCOCC#CCn1nc(-c2ccc(Cl)cn2)ccc1=O] | 0.017 |

TABLE 1-continued

Inhibition of Δ-9 fatty acid desaturase.

| Structure | I50 (µg/ml) |
|---|---|
| 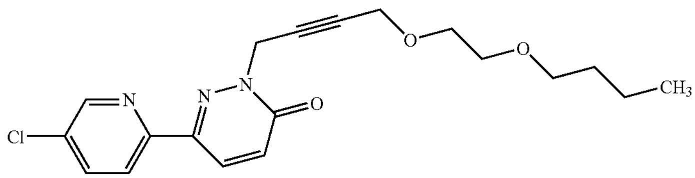 [SMILES: CCCCOCCOCC#CCn1nc(-c2ccc(Cl)cn2)ccc1=O] | 0.066 |
| 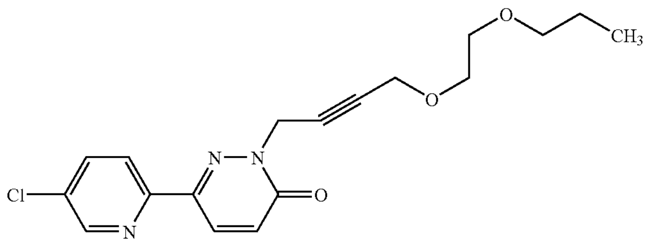 [SMILES: CCCOCCOCC#CCn1nc(-c2ccc(Cl)cn2)ccc1=O] | 0.039 |
| 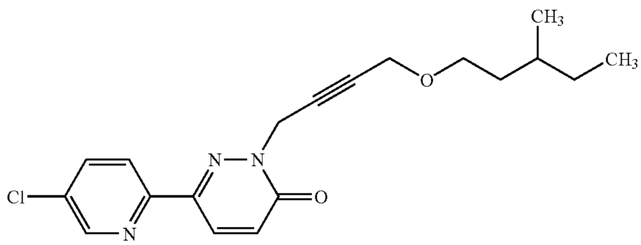 [SMILES: CCC(C)CCOCC#CCn1nc(-c2ccc(Cl)cn2)ccc1=O] | 0.152 |
| 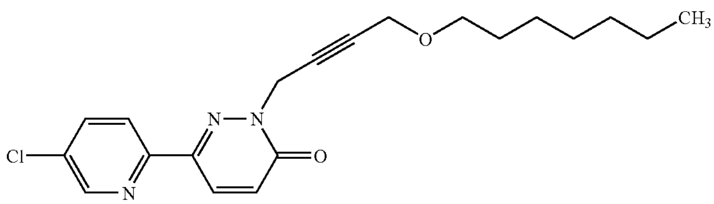 [SMILES: CCCCCCCOCC#CCn1nc(-c2ccc(Cl)cn2)ccc1=O] | 0.027 |
| 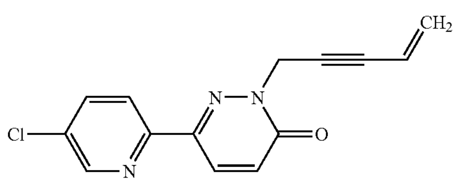 [SMILES: C=CC#CCn1nc(-c2ccc(Cl)cn2)ccc1=O] | 0.016 |
| 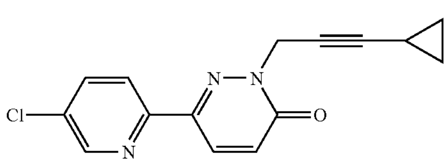 [SMILES: O=c1ccc(-c2ccc(Cl)cn2)nn1CC#CC1CC1] | 0.135 |
| 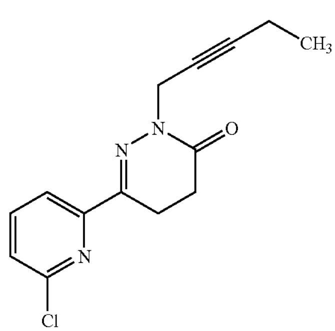 | >40 |

TABLE 1-continued

Inhibition of Δ-9 fatty acid desaturase.

| Structure | I50 (µg/ml) |
|---|---|
| (6-chloropyridin-2-yl)-2-(pent-2-yn-1-yl)pyridazin-3(2H)-one | 16.82 |
| (5,6-dichloropyridin-2-yl)-2-(pent-2-yn-1-yl)pyridazin-3(2H)-one | 0.081 |
| (3-chloropyridin-2-yl)-2-(pent-2-yn-1-yl)-4,5-dihydropyridazin-3(2H)-one | >40 |
| (3-chloropyridin-2-yl)-2-(pent-2-yn-1-yl)pyridazin-3(2H)-one | >40 |
| (3,5-dichloropyridin-2-yl)-2-(pent-2-yn-1-yl)-4,5-dihydropyridazin-3(2H)-one | >40 |
| (3,5-dichloropyridin-2-yl)-2-(pent-2-yn-1-yl)pyridazin-3(2H)-one | >40 |
| (5-chloropyridin-2-yl)-2-(6,6-dimethylhept-2-en-4-yn-1-yl)pyridazin-3(2H)-one | >40 |

TABLE 1-continued
Inhibition of Δ-9 fatty acid desaturase.
| Structure | I50 (µg/ml) |
|---|---|
| 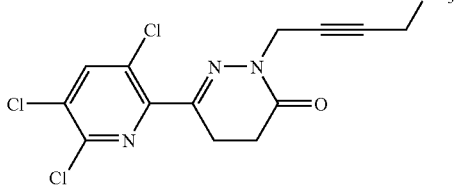 | >40 |
| 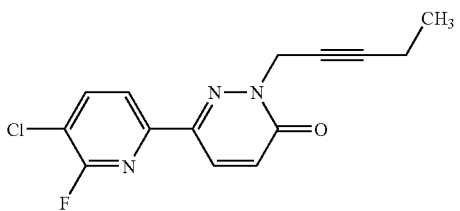 [SMILES: CCC#CCn1nc(-c2ccc(Cl)c(F)n2)ccc1=O] | 0.029 |
| 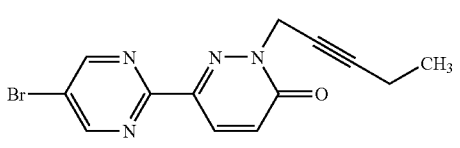 [SMILES: CCC#CCn1nc(-c2ncc(Br)cn2)ccc1=O] | 1.21 |
| 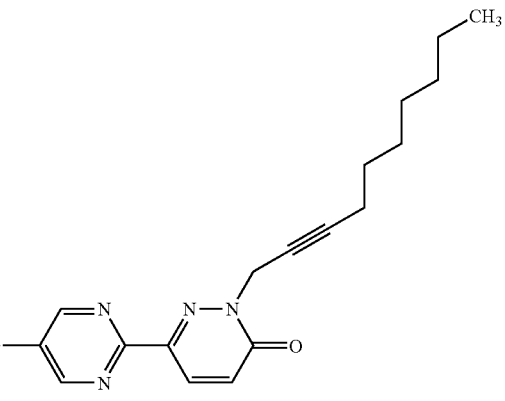 | 0.034 |
| 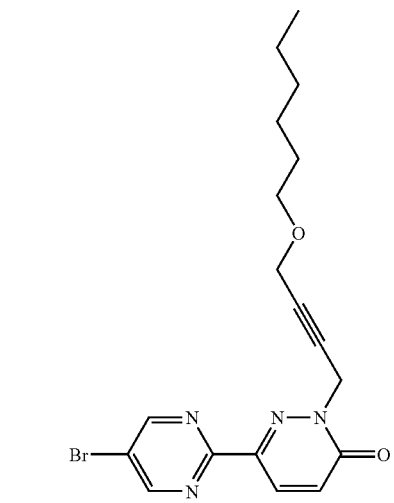 [SMILES: CCCCCCOCC#CCn1nc(-c2ncc(Br)cn2)ccc1=O] | 0.016 |

Example 2

Activity Towards Plant Pathogens

A glucose-yeast nitrogen base growth medium was used consisting of 20 g glucose, 3 g $K_2HPO_4$, 3 g $KH_2PO_4$ and 6.7 g yeast nitrogen base (without amino acids) per liter of water. Dilution series of test compound were prepared in 100 µl aliquots of YMP medium in 96-well microtiter plates. Wells were inoculated with 100 µl spore suspension of *Colletotrichum lagenarium* (COLLLA) or *Pyricularia oryzae* (PYRIOR) prepared in YMP medium at $2 \times 10^5$ spores per ml, and incubated at 25° C. for 72 h before assessing growth by reading plates in a NepheloStar plate reader. EC50 values (concentrations required for 50% inhibition of growth) were calculated from dose-response curves. EC50 values for fungitoxicity of compounds towards COLLLA and PYRIOR are shown in Table 2.

TABLE 2

Activity towards plant pathogenic fungi.

| Structure | EC50 COLLLA (ug/ml) | EC50 PYRIOR (ug/ml) |
|---|---|---|
| 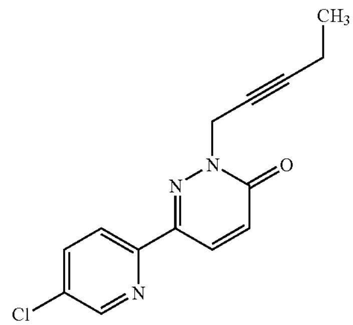 [SMILES: CCC#CCn1nc(-c2ccc(Cl)cn2)ccc1=O] | 0.113 | 0.0474 |
| 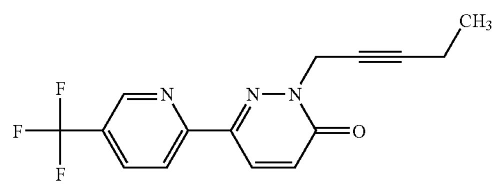 [SMILES: CCC#CCn1nc(-c2ccc(C(F)(F)F)cn2)ccc1=O] | 0.758 | 0.674 |
| 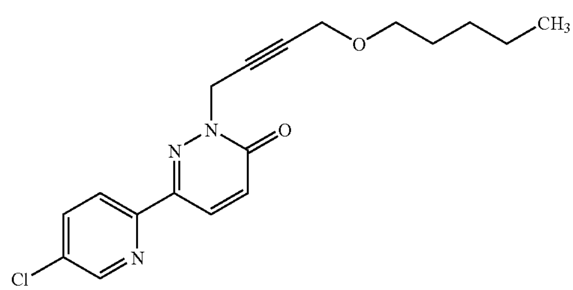 [SMILES: CCCCCOCC#CCn1nc(-c2ccc(Cl)cn2)ccc1=O] | 0.007 | 0.192 |
| 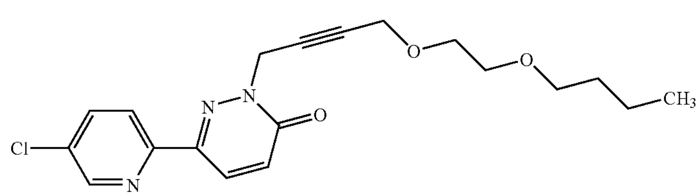 [SMILES: CCCCOCCOCC#CCn1nc(-c2ccc(Cl)cn2)ccc1=O] | 0.033 | 0.05 |
| 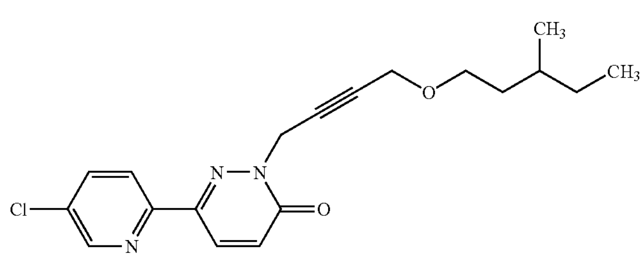 [SMILES: CCC(C)CCOCC#CCn1nc(-c2ccc(Cl)cn2)ccc1=O] | 1.16 | 0.284 |

TABLE 2-continued

Activity towards plant pathogenic fungi.

| Structure | EC50 COLLLA (ug/ml) | EC50 PYRIOR (ug/ml) |
|---|---|---|
| (5-chloropyridin-2-yl)-pyridazin-3(2H)-one with N-CH2-C≡C-cyclopropyl | 0.092 | 0.062 |
| (4-chloropyridin-2-yl)-4,5-dihydropyridazin-3(2H)-one with N-CH2-C≡C-CH2CH3 | 5.75 | 5.52 |
| (6-chloropyridin-2-yl)-4,5-dihydropyridazin-3(2H)-one with N-CH2-C≡C-CH2CH3 | 3.4 | 1.01 |
| (5-chloropyridin-2-yl)-4,5-dihydropyridazin-3(2H)-one with N-CH2-C≡C-CH2CH3 | 0.194 | 0.021 |
| (6-chloropyridin-2-yl)-pyridazin-3(2H)-one with N-CH2-C≡C-CH2CH3 | 1 | 1.4 |

TABLE 2-continued
Activity towards plant pathogenic fungi.
| Structure | EC50 COLLLA (ug/ml) | EC50 PYRIOR (ug/ml) |
|---|---|---|
| 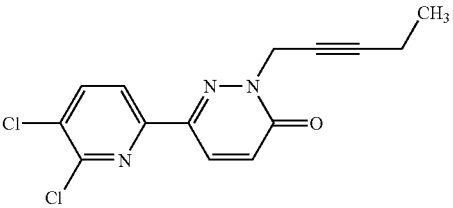 | 0.0537 | 0.0371 |
| 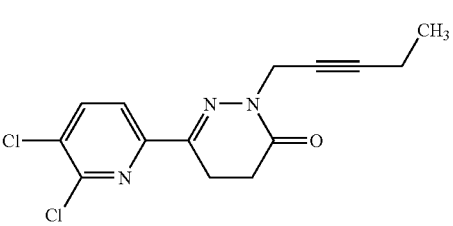 | 0.036 | 0.031 |
| 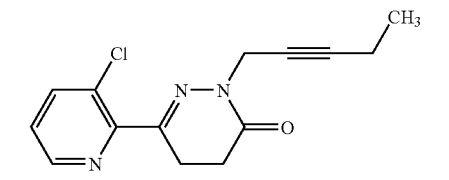 [SMILES: CCC#CCN1N=C(c2ncccc2Cl)CCC1=O] | >40 | 33 |
| 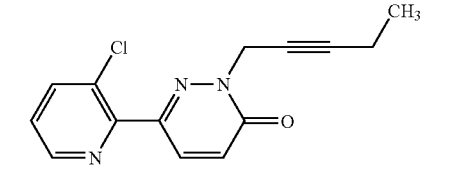 [SMILES: CCC#CCn1nc(-c2ncccc2Cl)ccc1=O] | >40 | >40 |
| 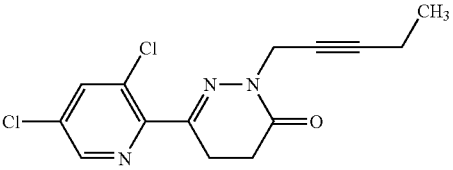 [SMILES: CCC#CCN1N=C(c2ncc(Cl)cc2Cl)CCC1=O] | 8 | 3.47 |
| 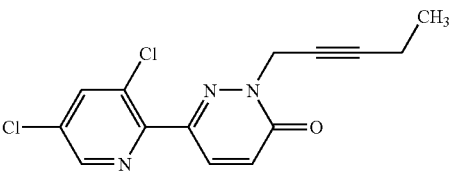 [SMILES: CCC#CCn1nc(-c2ncc(Cl)cc2Cl)ccc1=O] | 13.6 | 4.42 |
| 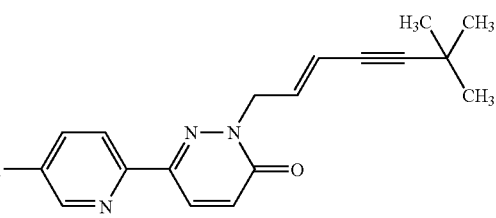 | >40 | 8.11 |

TABLE 2-continued

Activity towards plant pathogenic fungi.

| Structure | EC50 COLLLA (ug/ml) | EC50 PYRIOR (ug/ml) |
|---|---|---|
| [3,5,6-trichloropyridin-2-yl dihydropyridazinone with pent-2-ynyl] | 8.71 | 5.75 |
| [5-chloro-6-fluoropyridin-2-yl pyridazinone with pent-2-ynyl] | 0.048 | 0.0236 |
| [5-fluoro-6-fluoropyridin-2-yl pyridazinone with pent-2-ynyl] | 0.181 | 0.163 |

Example 3

Activity towards *Candida albicans*

Two-fold dilution series of compound were prepared in 100 µl aliquots of RPMI medium in 96-well microtiter plates. Wells were inoculated with 100 µl *C. albicans* cell suspension at $10^4$ cells/ml, and incubated at 35° C. for 48 h. Growth was quantified by reading the plates in a spectrophotometer at 490 nm and EC50 values were calculated from dose-response curves. EC50 values for fungitoxicity of compounds towards COLLLA and PYRIOR are shown in Table 3.

TABLE 3

| Activity towards Candida albicans | |
|---|---|
| Structure | EC50 (µg/ml) |
| [5-chloropyridin-2-yl pyridazinone with pent-2-ynyl] | 0.091 |
| [5-chloropyridin-2-yl pyridazinone with but-2-ynyl-O-pentyl chain] | 0.176 |

TABLE 3-continued

Activity towards Candida albicans

| Structure | EC50 (µg/ml) |
|---|---|
| 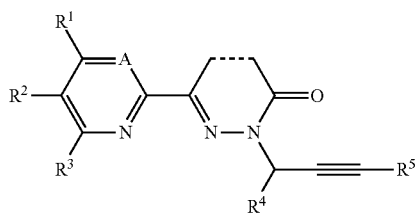 | 0.210 |

What is claimed is:

1. A compound of the formula

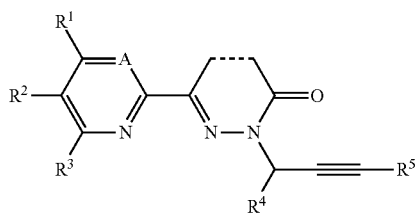

wherein

A represents N or $CR^6$;

-- represents one of a single and a double bond;

$R^1$, $R^2$, $R^3$ and $R^6$ independently represent H, halogen, nitro, cyano, $C_1$-$C_6$ alkyl, $C_1$-$C_6$ alkoxy, $C_1$-$C_6$ alkylthio, $C_1$-$C_6$ haloalkyl, $C_1$-$C_6$ haloalkoxy, $C_1$-$C_6$ haloalkylthio, unsubstituted or substituted phenyl, or unsubstituted or substituted phenoxy;

$R^4$ represents H, halogen, cyano or $C_1$-$C_6$ alkyl; and $R^5$ represents halogen, $C_1$-$C_8$ alkyl, $C_2$-$C_8$ alkenyl, $C_2$-$C_8$ alkynyl, $C_1$-$C_8$ alkoxy, $C_1$-$C_8$ haloalkyl, $C_2$-$C_8$ haloalkenyl, $C_2$-$C_8$ haloalkynyl or $C_1$-$C_8$ haloalkoxy with the proviso that when A represents N, then at least one of $R^1$, $R^2$, and $R^3$ represents halogen or $C_1$-$C_8$ haloalkyl, and when A represents $CR^6$, then at least one of $R^1$, $R^2$, $R^3$ and $R^6$ represents halogen or $C_1$-$C_8$ haloalkyl.

2. A fugicidal composition comprising a fungicidally effective amount of a compound of claim 1, in a mixture with an agriculturally acceptable adjuvant or carrier.

* * * * *